US010607724B2

(12) United States Patent
Miyauchi et al.

(10) Patent No.: US 10,607,724 B2
(45) Date of Patent: Mar. 31, 2020

(54) INFORMATION PROCESSING APPARATUS AND METHOD FOR CLINICAL LABORATORY MANAGEMENT

(71) Applicant: Sysmex Corporation, Kobe-shi, Hyogo (JP)

(72) Inventors: Akio Miyauchi, Kobe (JP); Naoki Tsuro, Kobe (JP); Norio Kowata, Kobe (JP); Naoki Kai, Kobe (JP); Shirou Kuwaoka, Kobe (JP); Yukihisa Minematsu, Kobe (JP); Mark Dahlberg, Elgin, IL (US); Steve Postma, Mundelein, IL (US); Chris Carrier, Cary, IL (US); Jackie Guenther, Flower Mound, TX (US); Anselm Mueller, Hamburg (DE)

(73) Assignee: SYSMEX CORPORATION, Hyogo (JP)

(*) Notice: Subject to any disclaimer, the term of this patent is extended or adjusted under 35 U.S.C. 154(b) by 586 days.

(21) Appl. No.: 15/233,361

(22) Filed: Aug. 10, 2016

(65) Prior Publication Data
US 2018/0046781 A1 Feb. 15, 2018

(51) Int. Cl.
G16H 10/40 (2018.01)
(52) U.S. Cl.
CPC .................... G16H 10/40 (2018.01)
(58) Field of Classification Search
None
See application file for complete search history.

(56) References Cited

U.S. PATENT DOCUMENTS 5,366,896 A * 11/1994 Margrey .......... G01N 35/00871
436/48
6,275,150 B1 * 8/2001 Mandler ................ G16H 40/63
340/525

(Continued)

FOREIGN PATENT DOCUMENTS

| EP | 0 970 655 A1 | 1/2000 |
| EP | 0 973 115 A2 | 1/2000 |
| WO | WO 03/102854 A2 | 12/2003 |

OTHER PUBLICATIONS

Managing your laboratory ecosystem—The Sysmex WAN Manager reports module, 2012, sysmex.com website (Year: 2012).*

(Continued)

Primary Examiner — Dennis W Ruhl
(74) Attorney, Agent, or Firm — Brinks Gilson & Lione

(57) ABSTRACT

To facilitate management of the entirety of one or a plurality of clinical laboratories. This information processing apparatus is used in management of a clinical laboratory in which an analyzer configured to analyze specimens is installed. The information processing apparatus includes: a communication section configured to communicate with a terminal operable by a user; and a controller configured to control display of the terminal via the communication section. On the basis of information collected from a plurality of analyzers installed in one or a plurality of clinical laboratories and from apparatuses relevant to the analyzers, the controller causes the terminal to display a screen including an index that indicates a status of the entirety of the one or the plurality of clinical laboratories. In response to the user selecting the index displayed in the screen, the controller causes the terminal to display the selected index so as to be divided in a plurality of categories.

33 Claims, 39 Drawing Sheets

(56) References Cited

U.S. PATENT DOCUMENTS

| | | | |
|---|---|---|---|
| 8,566,781 B2 | 10/2013 | DeMesa et al. | |
| 2006/0190187 A1 | 8/2006 | Mishima et al. | |
| 2007/0143046 A1* | 6/2007 | Budike, Jr. | G01D 4/004 |
| | | | 702/62 |
| 2007/0217949 A1 | 9/2007 | Mimura et al. | |
| 2008/0059441 A1* | 3/2008 | Gaug | G06F 16/951 |
| 2008/0312893 A1* | 12/2008 | Denton | G01N 35/00613 |
| | | | 703/11 |
| 2010/0094653 A1* | 4/2010 | Tribble | G06F 19/326 |
| | | | 705/3 |
| 2011/0161124 A1* | 6/2011 | Lappinga | G06Q 10/063 |
| | | | 705/7.11 |
| 2011/0320540 A1* | 12/2011 | Oostlander | G06F 11/3006 |
| | | | 709/206 |
| 2013/0047113 A1* | 2/2013 | Hume | G06Q 50/22 |
| | | | 715/771 |
| 2015/0278720 A1* | 10/2015 | Nye | G06Q 10/063 |
| | | | 705/7.11 |
| 2015/0331946 A1* | 11/2015 | Balwani | G16H 10/40 |
| | | | 707/769 |
| 2016/0020986 A1* | 1/2016 | Bosko | G06Q 10/20 |
| | | | 709/224 |
| 2017/0235448 A1* | 8/2017 | Kammath | G06F 3/0482 |
| | | | 715/736 |

OTHER PUBLICATIONS

"Sysmex America Achieves Clinical laboratory connectively milestone—200th Sysmex WAN middleware placement enables streamlined operations for hospitals nationwide", 2012, sysmex.com website (Year: 2012).*

Sysmex announces newest version of Clinical laboratory management software improves metrics reporting and operational efficiency, 2011, sysmex.com website (Year: 2011).*

Sysmex WAM v5.0 User Manual Hematology, Document No. 1036-MKT, www.sysmex.com (Jul. 2013) 287 pp.

Sysmex WAM v5.0 Release Notes, Document No. 62-1124, www.sysmex.com (Oct. 2013) 15 pp.

Sysmex WAM v5.0 Management Report Quick Guide, Sysmex America, Inc., www.sysmex.com (2014) 12 pp.

The Decision to refuse a European Patent Application dated May 23, 2019 in counterpart European patent application No. 17184445.9.

* cited by examiner

FIG. 9

ANALYZER ID: A

30a

| Data kind | Test item | Value | Timestamp | COLLECTED DATA |
|---|---|---|---|---|
| Processed specimen count | Item (1) hBs-Ag | 10 | 2016/7/5 AM10:00 | ... |
| | Item (2) hCV | 4 | 2016/7/5 AM10:00 | ... |
| | ... | ... | ... | ... |
| The number of re-runs | Item (1) hBs-Ag | 5 | 2016/7/1 PM 4:00 | ... |
| | Item (2) hCV | 0 | 2016/7/1 PM 4:00 | ... |
| | ... | ... | ... | ... |
| | | | | ... |

FIG. 10

ANALYZER ID: A

30a ↙ COLLECTED DATA

| Data kind | Error factor | Value | Timestamp | COLLECTED DATA |
|---|---|---|---|---|
| The number of re-runs | Reagent/consumable | 1 | 2016/7/1 PM 4:00 | ... |
| | Apparatus error | 3 | 2016/7/1 PM 4:00 | ... |
| | Measurement error | 1 | 2016/7/1 PM 4:00 | ... |
| | Panic value | 0 | 2016/7/1 PM 4:00 | ... |
| | ... | ... | ... | ... |
| Re-run ratio | Reagent/consumable | 1.27% | 2016/7/1 PM 4:00 | ... |
| | Apparatus error | 1.57% | 2016/7/1 PM 4:00 | ... |
| | Measurement error | 1.27% | 2016/7/1 PM 4:00 | ... |
| | Panic value | 0% | 2016/7/1 PM 4:00 | ... |
| | ... | ... | ... | ... |
| | | | | ... |

FIG. 12
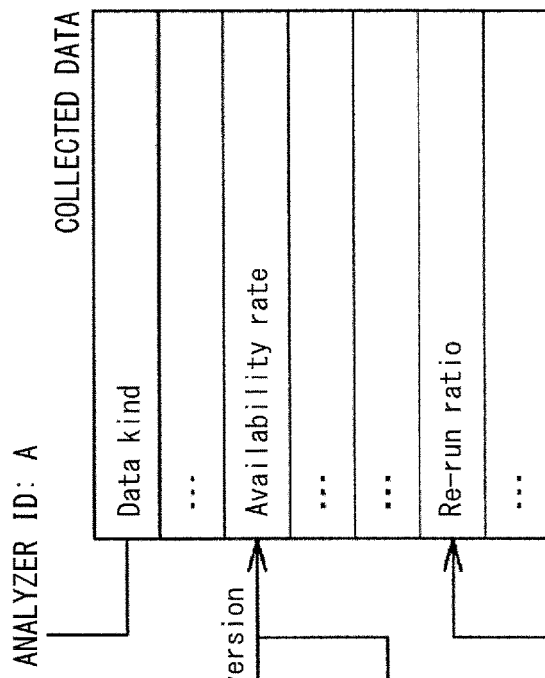
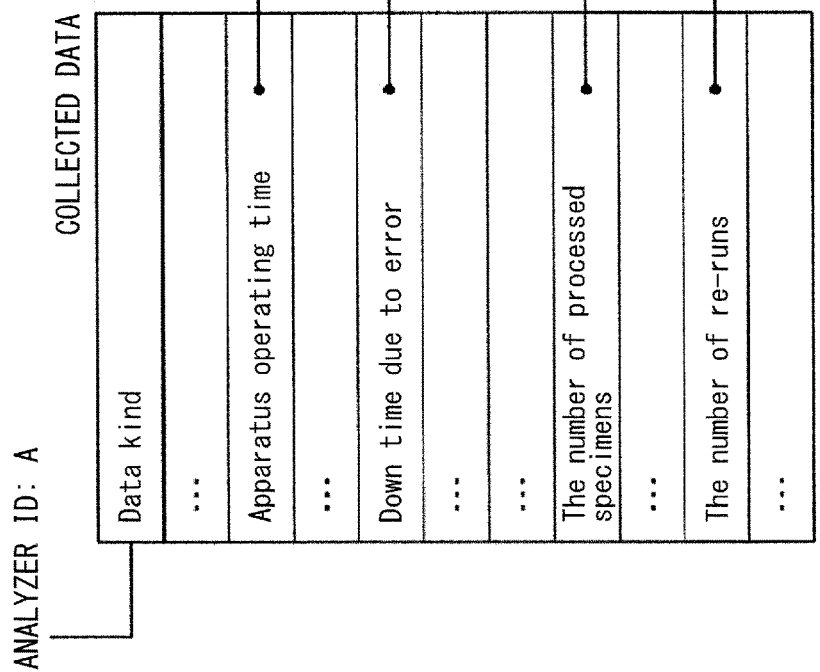

FIG. 13

GEOGRAPHIC INFORMATION 40b

| Area (1) | Area (2) | Area (3) | Area (4) | Apparatus ID |
|---|---|---|---|---|
| Japan | Kanto | Tokyo | Clinical laboratory: 1 | ID: A |
| | Kanto | Tokyo | Clinical laboratory: 1 | ID: B |
| | Kanto | Tokyo | Clinical laboratory: 1 | ID: C |
| | Kanto | Kanagawa | Clinical laboratory: 2 | ID: a |
| | Kanto | Kanagawa | Clinical laboratory: 3 | ID: b |
| | Kinki | Osaka | Clinical laboratory: 4 | ID: D |
| | Kinki | Osaka | Clinical laboratory: 4 | ID: E |
| | Tokai and hokuriku | Nagoya | Clinical laboratory: 5 | ID: F |
| | Hokkaido | Sapporo | Clinical laboratory: 6 | ID: c |
| | Tohoku | Sendai | Clinical laboratory: 7 | ID: d |
| | ... | ... | ... | ... |

FIG. 14

GEOGRAPHIC INFORMATION 40b

| Area (1) | Area (2) | Area (3) | ... | Area (4) | Apparatus ID |
|---|---|---|---|---|---|
| U.S.A | ... | ... | | ... | ... |
| | Colorado | Denver | | Clinical laboratory: 10 | ID: AA |
| | Colorado | Denver | | Clinical laboratory: 10 | ID: BB |
| | Colorado | Vail | | Clinical laboratory: 10 | ID: CC |
| | Indiana | Indianapolis | | Clinical laboratory: 20 | ID: aa |
| | Indiana | Indianapolis | | Clinical laboratory: 20 | ID: bb |
| | Virginia | Arlington | | Clinical laboratory: 40 | ID: DD |
| | Virginia | Arlington | | Clinical laboratory: 40 | ID: EE |
| | Illinois | Chicago | | Clinical laboratory: 50 | ID: FF |
| | Wisconsin | Green Bay | | Clinical laboratory: 60 | ID: cc |
| | Massachusetts | Boston | | Clinical laboratory: 70 | ID: dd |
| | | | | ... | ... |

FIG. 17B

| User's role | Application | Display settings |
|---|---|---|
| Multi-site management | Application ID: A1 | Display settings information: A11 |
| | Application ID: A2 | Display settings information: A21 |
| | Application ID: A3 | Display settings information: A31 |
| | ... | ... |
| Single site management | Application ID: a1 | Display settings information: a11 |
| | Application ID: a2 | Display settings information: a21 |
| | ... | ... |
| Clinical laboratory operation | Application ID: b1 | Display settings information: b11 |
| | Application ID: b2 | Display settings information: b21 |
| | ... | ... |
| | ... | |

SETTINGS INFORMATION (DISPLAY SETTING)

54a

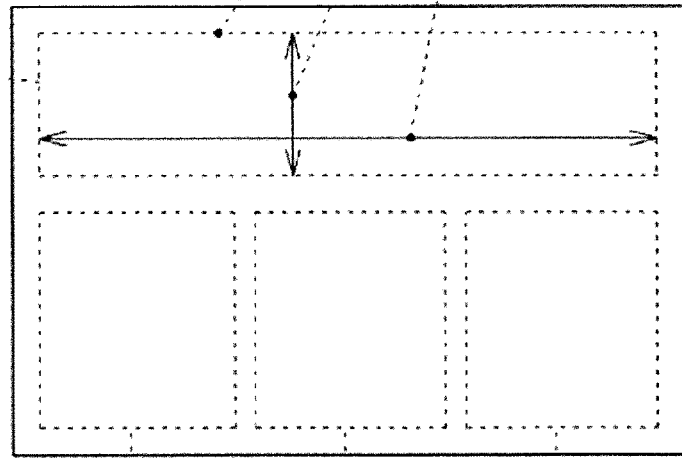

USER SETTINGS INFORMATION (ROLE SETTING)

| User | User's role | IP address |
|---|---|---|
| User ID: a001 | Multi-site management | Unlimited IP address |
| User ID: a003 | Single site management | ... |
| User ID: b001 | Clinical laboratory operation | ... |
| ... | ... | ... |

FIG. 18

USER SETTINGS INFORMATION (AREA SETTING) 54a

| User ID | User's area 1 | User's area 2 | User's area 3 | Analyzer ID |
|---|---|---|---|---|
| ... | ... | ... | ... | ... |
| ID: a001 | Kanto | Tokyo | Clinical laboratory: 1 | ID: A |
| | Kanto | Tokyo | Clinical laboratory: 1 | ID: B |
| | Kanto | Tokyo | Clinical laboratory: 1 | ID: C |
| | Kanto | Kanagawa | Clinical laboratory: 2 | ID: a |
| | Kanto | Kanagawa | Clinical laboratory: 3 | ID: b |
| ... | ... | ... | ... | ... |
| ID: a002 | Kinki | Osaka | Clinical laboratory: 4 | ID: D |
| | Kinki | Osaka | Clinical laboratory: 4 | ID: E |
| ID: b001 | Clinical laboratory: 5 | Null | Null | ID: F |

FIG. 20

| APPLICATION ID: A1 | APPLICATION MANAGEMENT INFORMATION | |
|---|---|---|
| Index to be displayed | Link destination | Display hierarchy |
| Re-run ratio: Daily<br>Definitive ratio: Daily<br>Positive ratio: Daily<br>Error ratio: Daily | Application ID: B1 | Null |

502a — Re-run ratio: Daily
502b — Definitive ratio: Daily
502c — Positive ratio: Daily
502d — Error ratio: Daily 52a

FIG. 21

| | The number of specimens | The number of re-runs | Re-run ratio | Positive ratio | Definitive ratio | Error | Cost | System Availability |
|---|---|---|---|---|---|---|---|---|
| ▶Total | 14,812 | 538 | 3.55% | 1.26% | 68% | 2.26% | △¥275,888 | 92% |
| ▶Hokkaido | 807 | 19 | 2.36% | 1.25% | 75% | 1.24% | △¥10,728 | 88% |
| ▶Tohoku | 1,412 | 22 | 1.56% | 1.13% | 55% | 1.28% | △¥18,774 | 92% |
| ▶Saitama | 1,694 | 205 | 12.10% | 1.22% | 61% | 1.18% | △¥67,586 | 92% |
| ▶Tokyo | 3,103 | 140 | 4.51% | 1.21% | 62% | 3.16% | △¥75,096 | 95% |
| ▶Tokai and hokuriku | 2,017 | 24 | 1.19% | 1.31% | 64% | 3.32% | △¥26,820 | 95% |
| ▶Kinki | 2,353 | 51 | 2.17% | 1.33% | 75% | 2.38% | △¥31,290 | 92% |
| ▶Chugoku and shikoku | 1,412 | 33 | 2.34% | 1.18% | 74% | 2.69% | △¥18,774 | 95% |
| ▶Kyushu | 2,017 | 44 | 2.18% | 1.43% | 77% | 2.83% | △¥26,820 | 90% |

Operation Status (Today)  Date:2016-03-31  APPLICATION ID: B1

FIG. 22

APPLICATION ID: B1

APPLICATION MANAGEMENT INFORMATION 52a

| Index to be displayed | Link destination | Display hierarchy | |
|---|---|---|---|
| | | First hierarchical rank | Second hierarchical rank |
| Re-run ratio: Daily | Null | First hierarchical rank | Second hierarchical rank |
| The number of re-runs: Daily | | First hierarchical rank | |
| Definitive ratio: Daily | | First hierarchical rank | |
| Positive ratio: Daily | | First hierarchical rank | |
| Error ratio: Daily | | First hierarchical rank | |
| Processed specimen count: Daily | | First hierarchical rank | |
| Cost: Daily | | | |
| System availability: Daily | | First hierarchical rank | |

FIG. 23

APPLICATION ID: B1-FIRST HIERARCHICAL RANK  APPLICATION MANAGEMENT INFORMATION

| Index to be displayed | | |
|---|---|---|
| Re-run ratio: Daily | Item (1) HBs-Ag | |
| | Item (2) HCV | |
| | ... | |
| The number of re-runs: Daily | Item (1) HBs-Ag | |
| | Item (2) HCV | |
| | ... | |
| ... | | |

| | The number of specimens | The number of re-runs | Re-run ratio | Positive ratio | Definitive ratio | Error | Cost | System Availability |
|---|---|---|---|---|---|---|---|---|
| ▶Total | 14,812 | 538 | 3.55% | 1.26% | 68% | 2.26% | △¥275,888 | 92% |
| ▼Hokkaido | 807 | 19 | 2.36% | 1.25% | 75% | 1.24% | △¥10,728 | 88% |
| TP | | 1 | 0.12% | 0.25% | 93% | 0.12% | △¥500 | |
| HBs-Ag | | 4 | 0.50% | 0.12% | 76% | 0.25% | △¥2,500 | |
| HBs-Ab | | 5 | 0.62% | 0.25% | 60% | 0.25% | △¥1,250 | |
| HCV | | 5 | 0.62% | 0.25% | 50% | 0.25% | △¥750 | |
| HTLV | | 1 | 0.12% | 0.12% | 80% | 0.12% | △¥4,128 | |
| HIV | | 2 | 0.25% | 0.00% | 76% | 0.00% | △¥600 | |
| B19 | | 1 | 0.12% | 0.25% | 91% | 0.25% | △¥980 | |

FIG. 30

| User | Disclosure to third party permitted ? |
|---|---|
| User ID: a001 | Yes |
| User ID: a003 | No |
| User ID: b001 | Yes |
| ... | |

| User | User to whom disclosure is permitted |
|---|---|
| User ID: a001 | User ID: a003 |
| | User ID: a004 |
| | User ID: b001 |
| | ... |
| User ID: a003 | User ID: a001 |
| | User ID: d001 |
| | ... |
| User ID b001 | User ID: a001 |
| | User ID: e003 |
| | ... |
| | ... |

FIG. 34

| Proficiency Test Score | Date: 2016-03-31 | | | | | | | |
|---|---|---|---|---|---|---|---|---|
| Jone Smith <br> Area Manager | | | | | | | | |
| Hematology-CBC <br> Competency Test Requirement | 2015 Score | Report | 2014 Score | Report | 2013 Score | Report | 2012 Score | Report |
| Direct Observation patient testing | 80 | | 80 | | 80 | | 80 | |
| Recording and Reporting of test result | 65 | 📄 | 80 | | 80 | | 70 | 📄 |
| Review of worksheets, quality control proficiency testing result and maintenance records | 80 | | 80 | | 80 | | 80 | |
| Direct observation of maintenance and function checks | 80 | | 65 | 📄 | 55 | 📄 | 80 | |
| Previously analyzed samples, proficiency testing materials of internal blind samples | 35 | 📄 | 80 | | 80 | | 80 | |
| Problem solving | 80 | | 80 | | 80 | | 10 | 📄 |

FIG. 36

| FIELD | BIOCHEMISTRY |

UNPROCESSED SPECIMEN LIST

| | ANALYZER A | ANALYZER B | ANALYZER C |
|---|---|---|---|
| 01-0501-00001 TARO OSAKI | | FINISHED | |
| 01-0501-00003 JIRO GOTANDA | NOT FINISHED | | |
| 01-0501-00007 SABURO MEGURO | | NOT FINISHED | |
| 01-0501-00011 SHIRO HARAJUKU | | RETEST | |

INFORMATION PROCESSING APPARATUS AND METHOD FOR CLINICAL LABORATORY MANAGEMENT

BACKGROUND OF THE INVENTION

1. Field of the Invention

The present invention relates to information processing apparatuses and methods for managing clinical laboratories.

2. Description of the Related Art

Japanese Laid-Open Patent Publication No. H8-233825 discloses a data management apparatus which receives measurement data of quality control measurement and measurement data of patient specimens from each of a plurality of analyzers installed in clinical laboratories in a facility such as a hospital and a medical institution, and which indicates, on a single monitor screen, normality or abnormality of each measurement data associated with its corresponding analyzer. As the monitor screen, a screen as shown in FIG. 35 is displayed. This data management apparatus is configured to display, for each measurement field and on a single step-management screen, the measurement progress status of each analyzer so as to be associated with the analyzer and with its corresponding specimens. As the step-management screen, a screen as shown in FIG. 36 is displayed.

SUMMARY OF THE INVENTION

With the monitor screen and the step-management screen mentioned above, it is possible to ascertain measurement data, measurement progress, and the like for each analyzer, but it is difficult to ascertain the operating status, the analysis status, and the like of apparatuses in the entirety of the clinical laboratory. In particular, when managing a plurality of clinical laboratories, it is difficult to ascertain such statuses.

One mode of the present invention is an information processing apparatus to be used in management of a clinical laboratory in which an analyzer configured to analyze specimens is installed. In an embodiment, the information processing apparatus includes a communication section configured to communicate with a terminal operable by a user, and a controller configured to control display of the terminal via the communication section.

The controller is configured to execute a process of causing, on the basis of information collected from a plurality of analyzers installed in one or a plurality of clinical laboratories or from apparatuses relevant to the analyzers, the terminal to display a screen including an index that indicates a status of an entirety of the one or the plurality of clinical laboratories. Since such an index is displayed, the user can easily ascertain the status of the entirety of the one or the plurality of clinical laboratories. It is sufficient that the index is an index useful for ascertaining the status of the entirety of such clinical laboratories. The index may be: an index regarding a plurality of analyzers or apparatuses relevant to the analyzers; an index that indicates the status of tests performed in the clinical laboratories; an index regarding the staff of the clinical laboratories; or an index regarding a reagent or another article, or regarding software or the like used in the clinical laboratories.

The controller is configured to be able to execute a process of causing, in response to the user selecting the index displayed in the screen, the terminal to display the selected index so as to be divided in a plurality of categories. The divisions in a plurality of categories may be divisions for respective apparatuses such as analyzers installed in the clinical laboratories, may be divisions for respective indexes that each indicate clinical laboratory performance (TAT or the like), may be divisions each for a plurality of regions that the clinical laboratory administrator is in charge of, may be divisions for respective test items for analyzers, or may be divisions for respective abnormality factors in analyzers, for example.

By displaying the selected index so as to be divided in a plurality of categories, the user can obtain more detailed information regarding the selected index after ascertaining the status of the entirety of the clinical laboratories. Thus, the user can easily obtain information necessary for clinical laboratory management. Thus, the user can take various measures for keeping appropriate states of the clinical laboratories.

Another mode of the present invention is a management method for a clinical laboratory in which an analyzer configured to analyze specimens is installed. The management method includes, on the basis of information collected from a plurality of analyzers installed in one or a plurality of clinical laboratories or from apparatuses relevant to the analyzers, displaying to a user a screen including an index that indicates a status of an entirety of the one or the plurality of clinical laboratories; and in response to the user selecting the index displayed in the screen, displaying to the user the selected index so as to be divided in a plurality of categories.

Another mode of the present invention is a computer program including commands for causing a processor of a computer to execute the above management method. The computer program is stored in a computer-readable storage medium.

BRIEF DESCRIPTION OF THE DRAWINGS

FIG. 9 is a data structure diagram of collected data;

FIG. 10 is a data structure diagram of collected data;

FIG. 12 is an explanatory diagram of conversion of collected data;

FIG. 13 is a data structure diagram of geographic information;

FIG. 14 is a data structure diagram of geographic information;

FIG. 17B is a data structure diagram of the settings-information;

FIG. 17C is a data structure diagram of the settings-information;

FIG. 18 is a data structure of the settings-information;

FIG. 20 is a data structure diagram of application management information;

FIG. 21 is a display screen realized by an application;

FIG. 22 is a data structure diagram of the application management information;

FIG. 23 is a data structure diagram of the application management information;

FIG. 25 is a display screen realized by an application;

FIG. 30 is a data structure diagram of the settings-information;

FIG. 32 is a data structure diagram of the settings-information;

FIG. 34 is a display screen realized by an application;

FIG. 36 is a schematic diagram showing a step management screen according to conventional art.

DETAILED DESCRIPTION OF THE PREFERRED EMBODIMENTS

[1. Management System]

Figure 1:
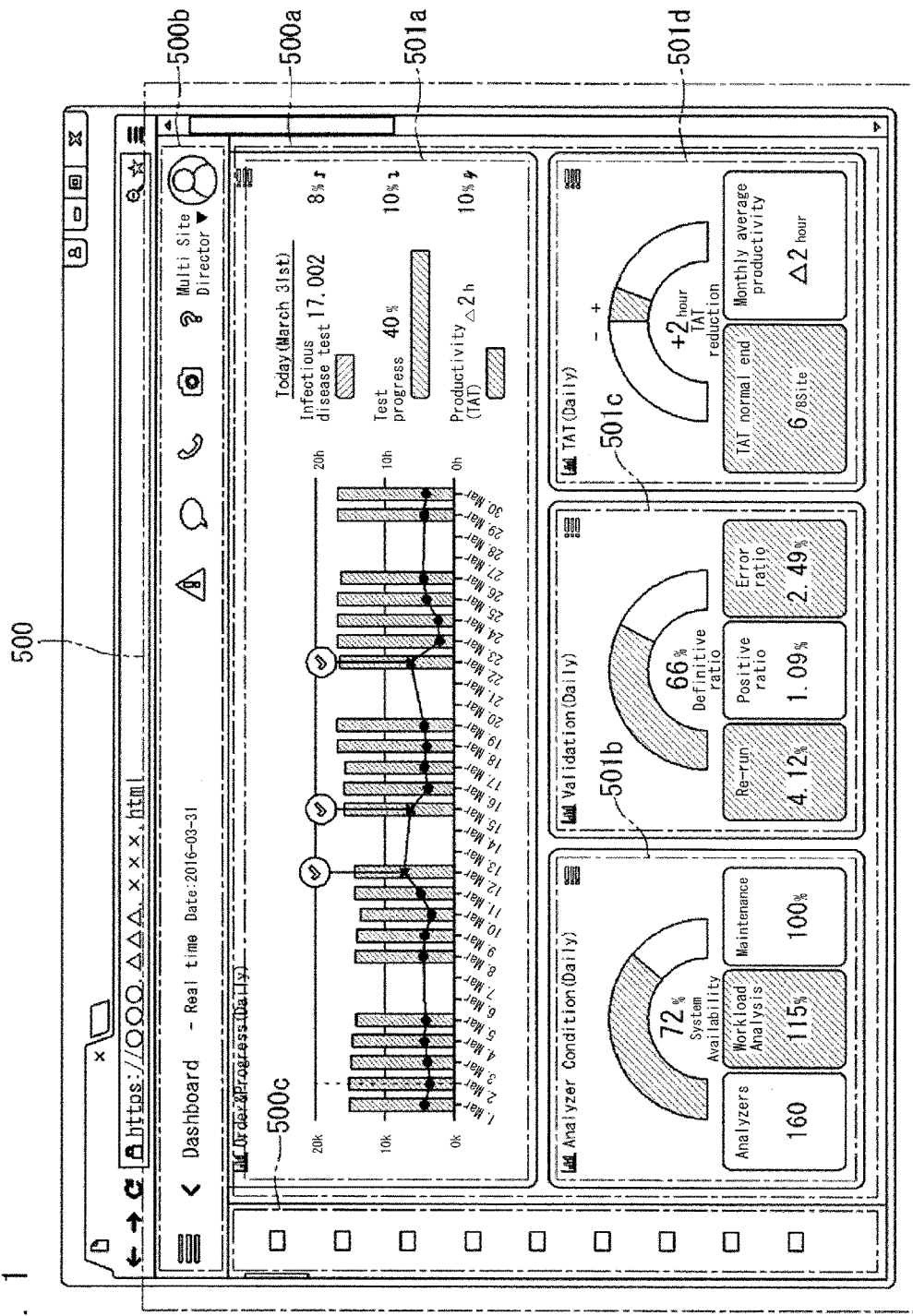
FIG. 1 is a display screen displayed by a Web browser.

FIG. 1 shows a display screen 500 displaying management information for clinical laboratory management. In this embodiment, the display screen 500 is displayed by a browser of a terminal 6 operated by a user who is an administrator of a clinical laboratory, for example. The display screen 500 has a plurality of display regions 500a, 500b, and 500c, for example.

The display region 500a may occupy the most part of the display screen 500. In the display region 500a, a dashboard shown in FIG. 1 is displayed, for example. A dashboard 500a displays one or a plurality of widgets 501a, 501b, 501c, and 501d. The widgets 501a, 501b, 501c, and 501d are applications 501a, 501b, 501c, and 501d displayed on the dashboard 500a. Each widget causes its corresponding application 501a, 501b, 501c, 501d, to be displayed in a form of an icon. Each application displayed in a form of an icon includes display of at least one index for clinical laboratory management. Each index indicates the status of the entirety of one or a plurality of clinical laboratories, for example. To "display in a form of an icon" means to "display a figure that is selectable through an operation made by a user". In the display region 500a, things other than the dashboard 500a may be displayed.

The display region 500b is located in an upper portion of the display screen 500, displays the state of the screen, and displays icons for screen operation. The display region 500c is located on the left side of the display screen 500, and displays icons for screen operation. The contents displayed in the display region 500a can be changed through an operation made in the display region 500b, 500c, or through operation made in the display region 500a. It should be noted that the operation includes clicking with a mouse or tapping the screen of a touch panel.

The widgets 501a, 501b, 501c, and 501d shown in FIG. 1 are applications regarding clinical laboratory management. Each application 501a, 501b, 501c, 501d displays one or a plurality of indexes indicating the status of the entirety of one or a plurality of clinical laboratories. The plurality of applications 501a, 501b, 501c, and 501d display different indexes, respectively. In the dashboard 500a, pieces of management information including various indexes are collectively arranged and displayed. Thus, by referring to the dashboard 500a, the administrator of such clinical laboratories can easily obtain operation information and alert information necessary for clinical laboratory management, and can easily ascertain the status of the entirety of the clinical laboratories.

The display screen 500 shown in FIG. 1 is for an administrator who manages a plurality of clinical laboratories (multiple sites). For the multi-site administrator, in the dashboard 500a, indexes are displayed that have been calculated on the basis of information collected from a plurality of clinical laboratories of which the administrator is in charge.

In the dashboard 500a shown in FIG. 1, four applications 501a, 501b, 501c, and 501d are displayed. In FIG. 1, each application displays a plurality of indexes. In the dashboard 500a, more applications can be displayed.

The application 501a (Order & Progress (Daily)) in FIG. 1 daily displays the number of test orders and indexes regarding the progress status. The bar graph in the application 501a shows the number of specimens for which test orders have been received for each day. The line graph shows the turnaround time (TAT) per specimen. Each check mark in the graph shows that the TAT of that day has exceeded a reference time. "Infectious disease test 17,002" in the application 501a indicates the number of test items for which test orders have been received. "Test progress 40%" in the application 501a indicates the proportion of the number of test items for which the tests have been completed at the time when the display is made, relative to the number of test items for which the test orders had been received. "Productivity (TAT) Δ2h" in the application 501a indicates that the TAT per specimen of the day is 2 hours shorter than the reference time.

The application 501b (Analyzer Condition (Daily)) displays indexes regarding the state of analyzers 10, such as an availability rate. The availability rate is calculated by dividing an apparatus operating time by the sum of the apparatus operating time and a down time due to error.

The application 501c (Validation (Daily)) displays indexes regarding validation such as definitive ratio, re-run ratio, positive ratio, and error ratio. The definitive ratio indicates the proportion of normal specimens having normal analysis results. The re-run ratio indicates the proportion for which re-run has been conducted. The error ratio indicates the proportion of errors that have occurred. The application 501d (TAT (Daily)) displays indexes regarding the turnaround time. In the application 501d, "+2 hour TAT reduction" indicates that the TAT has been reduced by 2 hours. "TAT normal end 6/8 Site" indicates that the TATs of six clinical laboratories in eight clinical laboratories are shorter than the reference time. "Monthly average productivity Δ2 hour" indicates that the average TAT of that month is shorter than the reference time by 2 hours.

In FIG. 1, the value of each index displayed by its corresponding application is calculated on the basis of information collected from a plurality of clinical laboratories of which the administrator is in charge. Thus, by referring to the dashboard 500a, the administrator can ascertain the status of the clinical laboratories in the entirety of the area of which the administrator is in charge. Each index in the present embodiment is for clinical laboratory management. In order for the administrator to manage clinical laboratories, it is useful not only to ascertain the status of individual analyzers, but also to ascertain the status of the entirety of the clinical laboratories. The status of the entirety of the clinical laboratories includes the status of staff of the clinical laboratories, the status of stocks in the clinical laboratories, and the like, in addition to the operation status of the clinical laboratories. The indexes in the present embodiment can include various indexes for clinical laboratory management.

Hereinafter, examples of indexes that can be displayed in the dashboard 500a and the like are shown. The indexes below also include the indexes shown in FIG. 1. The indexes below are calculated by applications. The indexes below can be displayed also on a screen shifted from the dashboard 500a. The indexes below are examples of indexes indicating the status of the entirety of the clinical laboratories.

The indexes can include Turnaround Time (TAT). TAT is the time taken in processing one specimen, for example. TAT is calculated as the time taken in processing one specimen, per analyzer or per clinical laboratory, for example. The time taken in the processing is calculated as an average time, for example. TAT in the present embodiment means the time from collection of a specimen from a patient, through a pre-treatment step, a specimen analysis step, and a re-run step, to determination of a test result. The pre-treatment step is a step of pre-treating a specimen for the specimen analysis step, and includes a centrifugation process, a stopper-opening process, a specimen dispensing process, and the like. The specimen analysis step is a step in which the specimen is analyzed by an analyzer 10. The re-run step is a step of re-analyzing the specimen. TAT in the present embodiment is calculated, for example, on the basis of the specimen collection time obtained from LIS described later, the time of pre-treatment step obtained from Sysmex WAM (trademark) described later, and the specimen analysis time and the re-run time obtained from the analyzer 10 described later.

The indexes may include "TAT for each process step (hereinafter, Process step TAT)", which is an index representing a subdivision of TAT. Process step TAT can include, for example, First-step TAT, Second-step TAT, Third-step TAT, and Fourth-step TAT. First-step TAT indicates the time taken in collecting blood from a patient, for example. Second-step TAT indicates the time taken in performing pre-treatment on the specimen, for example. Third-step TAT indicates the time from when the specimen was set in the analyzer 10 to when the test result was outputted. Fourth-step TAT indicates the time taken in re-run for the specimen, for example. The indexes may include TAT for each measurement item, which is an index representing a subdivision of TAT for each measurement item. Each measurement item is a measurement item used in the analyzer.

The indexes can include Workload Analysis (load status in analysis status). Workload Analysis is the number of actually received test orders, relative to the specimen processing capacity. For example, in a case where the specimen processing capacity per day is 100 specimens, if the number of actually received test orders per day is 120 specimens, Workload is 120%. The specimen processing capacity is the number of specimens that can be processed in a clinical laboratory. For example, it is assumed that a clinical laboratory has two analyzers, and each analyzer can process 200 specimens per hour, and each analyzer operates 7 hours per day. Then, the specimen processing capacity per day of the clinical laboratory is: 200×2×7=2800 specimens. The specimen processing capacity may be the number of specimens that can be processed by an analyzer.

The indexes can include, as further detailed indexes for Workload, MaxN/hour (the maximum value of the number of specimen processable cases (N) per hour), Total number of processable cases per day, and Peak over per xxx (xxx=Day/Week, etc.). Peak means that Workload per hour has exceeded 100%. Peak over per xxx is the number of times by which Workload per hour has exceeded 100%. "xxx" is a period, and one day, one month, or one year, for example.

The indexes may include System Availability (Availability). Availability means the degree by which the analyzers and the like can operate. Availability is expressed as Availability rate, for example. As described above, the availability rate of an apparatus is calculated by dividing an apparatus operating time by the sum of the apparatus operating time and a down time due to error. The sum of the apparatus operating time and the down time due to error is the time during which the apparatus should be usable. The apparatus operating time is the time during which the apparatus was actually usable. When the time during which the apparatus should be usable is known, the availability may be expressed as the time during which the apparatus was actually usable. As further detailed indexes for Availability, Availability per analyzer, Availability per site such as a clinical laboratory, and Availability per multiple sites.

The indexes can include Analyzer Condition (the state of the analyzer). As the state of the analyzer, Analyzer Condition indicates OK or NG, or whether or not the valid period has expired, for example. NG corresponds to a case where an error of the analyzer, a QC abnormality, or a communication abnormality has occurred, for example.

The indexes can include QC Control (OK or Err) as a further detailed index for Analyzer Condition. QC Control is an index for internal quality control, and indicates whether or not a measurement value is within an allowable range relative to the average value for Quality Control (QC) determined in the own facility (or whether or not a difference between the measurement value and a reference value is greater than or equal to a predetermined value).

The indexes can include QC External (OK or Err) as a further detailed index for Analyzer Condition. QC External is an index for external quality control, and indicates whether or not a measurement value is within an allowable range, by comparing a QC result of the own facility and the average value of the population composed of a plurality of facilities.

The indexes can include System Status (OK or Err) as a further detailed index for Analyzer Condition. System Status indicates whether or not a predetermined error/warning has occurred in the analyzer (for example, a door for reagent insertion is left open, etc.).

The indexes can include Service (yy/mm/dd) as a further detailed index for Analyzer Condition. Service indicates the latest maintenance date on which maintenance of the analyzer was conducted, for example. When a predetermined period or longer has elapsed from the maintenance date, a warning is issued (the color of the icon is changed, etc.).

The indexes can include System Availability (%) as a further detailed index for Analyzer Condition. System Availability is as described above.

The indexes can include Calibration (yy/mm/dd) as a further detailed index for Analyzer Condition. Calibration indicates the latest calibration date on which calibration was conducted, for example. When a predetermined period or longer has elapsed from the latest calibration date, a warning is issued (the color of the icon is changed, etc.).

The indexes can include Multi-Site Workload (load status in analysis status). Multi-Site Workload indicates a value (average value or the like) calculated from loads at a plurality of sites.

The indexes can include Multi-Site TAT. Multi-Site Workload indicates a value (average value or the like) calculated from TATs at a plurality of sites.

The indexes can include Cyclecount Balance. Cyclecount Balance indicates comparison of the number of times of measurement sequence conducted (Cyclecount) by each of a plurality of analyzers in a site. Cyclecount Balance is useful for ascertaining whether the Cyclecount weighs heavily on a specific analyzer in the site.

The indexes can include the number of processed specimens per analyzer as a further detailed index for Cyclecount Balance.

The indexes can include Validation. Validation is an index regarding operation validation for the operating status of analyzers and clinical laboratories, and also serves as an index regarding the abnormality occurrence status of analyzers and clinical laboratories.

The indexes can include the number of re-runs (Re-run number) or Re-run ratio as a further detailed index for Validation. The number of re-runs is the number by which re-run was conducted. Re-run ratio is a value obtained by dividing the number of re-runs by the number of processed specimens.

The indexes can include Positive ratio as a further detailed index for Validation. Positive ratio is the proportion of specimens whose test results are positive.

The indexes can include Definitive ratio as a further detailed index for Validation. Definitive ratio is the definitive ratio of test results.

The indexes can include the number of errors or Error ratio as a further detailed index for Validation. The number of errors is the number of occurrence of errors in tests, and Error ratio is a value obtained by dividing the number of errors by the number of processed specimens.

The indexes can include Cost as a further detailed index for Validation. Cost is lost profits due to errors and re-runs. On the basis of pecuniary information (the amount of profits per hour, the amount of sales per hour, etc.) per test item, the amount of money that could have been obtained if tests had been conducted during the time taken in re-runs or during the time in which tests could not be conducted due to errors, is calculated as cost.

The indexes can include System Availability (%) as a further detailed index for Validation. System Availability is as described above.

It should be noted that the applications displayed in the dashboard 500a may include applications other than the applications for displaying indexes. For example, in the dashboard 500a, a widget for benchmark may be displayed. The benchmark is for comparing, with respect to a predetermined index (for example, any one of the indexes described above), the site managed by the administrator himself/herself with a site managed by another person. The benchmark will be described later.

Figure 2:
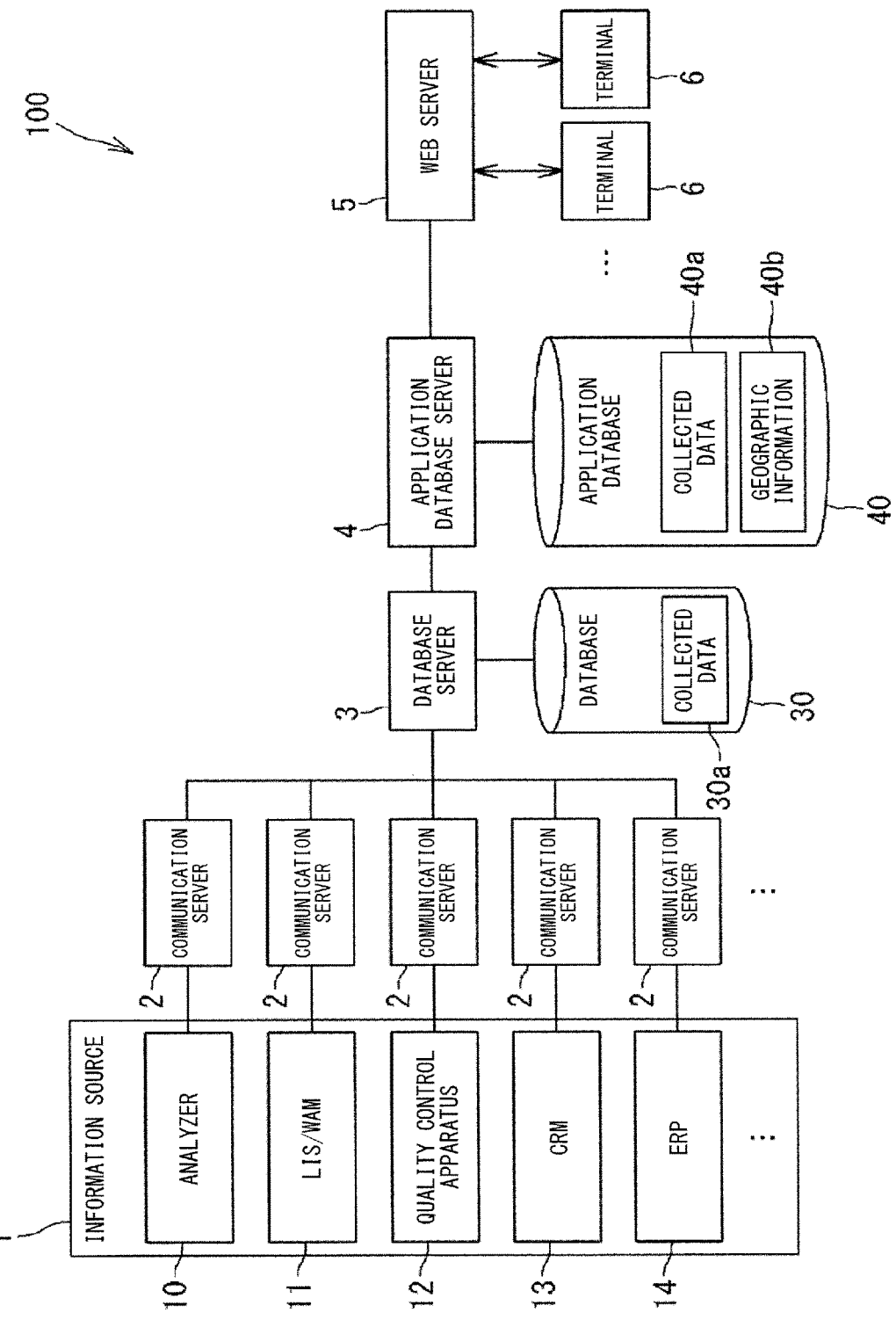
FIG. 2 is a configuration diagram of a management system.

FIG. 2 shows a management system 100 which includes a Web server 5 for generating the display screen 500 shown in FIG. 1. The Web server 5 is an information processing apparatus to be used in clinical laboratory management. The Web server 5 displays management information customized for each of a plurality of administrators whose roles are varied.

The management system 100 collects information regarding a plurality of clinical laboratories via a computer network such as the Internet. Each clinical laboratory is a place where specimens are analyzed. Each clinical laboratory is provided in a medical facility such as a hospital, for example. In each clinical laboratory, one or a plurality of analyzers 10 are installed. Each analyzer 10 analyzes specimens. Each specimen is a clinical specimen such as blood or tissue collected from a patient. The plurality of analyzers 10 may respectively be analyzers which analyze specimens for at least one common test item. For example, the plurality of analyzers 10 may respectively be analyzers which are of the same kind and which analyze specimens for a plurality of common test items. The plurality of analyzers 10 may be analyzers which analyze specimens for different test items, respectively.

In some cases, in a clinical laboratory, an apparatus relevant to an analyzer is installed. Hereinafter, an apparatus relevant to an analyzer will be referred to as "relevant apparatus". The relevant apparatus may be installed outside the clinical laboratory.

The relevant apparatus may be an apparatus 11 which gives an operation command to an analyzer 10 and which obtains an analysis result from the analyzer 10. The apparatus 11 may be Laboratory Information System (LIS) and Sysmex WAM (trademark), for example. The LIS has stored therein the collection time of each specimen, for example. The Sysmex WAM has stored therein the time of pre-treatment step, for example. The relevant apparatus may be a quality control apparatus 12. The quality control apparatus 12 obtains a measurement result of a quality control sample from the analyzer 10 and manages the quality of the analyzer 10. The relevant apparatus may be a CRM (Customer Relationship Management) apparatus 13, or may be an ERP (Enterprise Resource Planning) apparatus 14. The CRM apparatus 13 conducts matching among a user ID, facility information such as a clinical laboratory, information of the apparatuses 10, 11, and 12, and configures a time stamp, etc., for generating TAT and error information received from a facility such as a clinical laboratory. The ERP apparatus 14, if provided with a reagent automatic ordering application, such as for order management, for example, performs matching between reagent ordering information and facility information, and generates information of product sending procedure progress, shipment number, and invoice. The information from the ERP apparatus 14 is used for adding information to an ordered product such as reagent name indicated on the dashboard, for example. The CRM apparatus 13 and the ERP apparatus 14 are IT systems for users, but in general, are set not in the user-side clinical laboratory but on the system provider side.

The analyzer 10 and the relevant apparatuses 11, 12, 13, and 14 serve as an information source 1 for information to be collected in the management system 100. The collected information is, for example, information regarding the operation status of the clinical laboratory or the operation status of the analyzer. The collected information is used in generation of management information. In the present embodiment, indexes calculated from information collected from a plurality of information sources 1 including the analyzer 10 and the relevant apparatuses 11, 12, 13, and 14 is collectively displayed on a single display region which is the dashboard 500a. Thus, the user can easily ascertain the status of the entirety of the clinical laboratory based on the information from the plurality of apparatuses 10, 11, 12, 13, and 14, by referring to a single display region 500a.

The terminal 6 as mentioned above is operated by a user of the system 100. The user mainly assumed is an administrator of a clinical laboratory, but not limited to such an administrator, and the user may be any person that needs to ascertain the status of the clinical laboratory, such as a laboratory technician in the clinical laboratory, a person in charge of the manufacturer that provides the system 100, or the like. The administrator manages one or plurality of clinical laboratories. The role of the administrator is different, depending on the administrator. Examples of the administrator include an administrator who manages a clinical laboratory of only one medical facility, and an administrator who manages clinical laboratories of a plurality of medical facilities. Further, in some cases, the geographic ranges in charge are different depending on the administrators. Furthermore, even in a case of managing the same clinical laboratory, a person may be responsible for comprehensive management of the clinical laboratory, and another person may be responsible only for tests, for example. In this manner, the roles of administrators are varied. The Web server 5 generates management information according to the role of the administrator, and causes the terminal 6 to display the management information.

The management system 100 includes communication servers 2. Each communication server 2 is a server which functions as a gateway through which the information source 1 accesses the management system 100. The communication server 2 transfers information transmitted from the information source 1, to a server 3.

The management system 100 includes a database server 3. The server 3 integrates information collected from the information source 1 into a uniform format, and stores the integrated information, as collected data 30a, into a database 30. Even when the format of information transmitted by the apparatuses 10, 11, 12, 13, and 14 serving as the information source 1 are different, those pieces of information are converted by the server 3 into the collected data 30a having the uniform format. For example, the specimen collection time collected from the LIS, the time of pre-treatment step collected from the Sysmex WAM (trademark), the specimen analysis time and the re-run time collected from the analyzer 10 described later have different formats respectively, but are integrated by the server 3 into a uniform format, to be stored in the database 30.

The management system 100 includes an application database server 4. The server 4 converts the collected data 30a stored in the database 30, into collected data 40a in a form that is appropriate for indexes to be provided by the Web server 5 to the terminal 6. The converted collected data 40a is stored in an application database 40. For example, on the basis of the collected data 30a, such as the specimen collection time, the time of pre-treatment step, the specimen analysis time, the re-run time, and the like of a certain clinical laboratory, the server 4 calculates TAT of that clinical laboratory. The database 40 also has geographic information 40b that indicates the areas in which the apparatus 10, 11, 12, 13, and 14 are installed. On the basis of the collected data 40a stored in the database 40, the Web server 5 generates management information including indexes for clinical laboratory management. The Web server 5 calculates the value of each index by also using the geographic information 40b as necessary.

Figure 3:
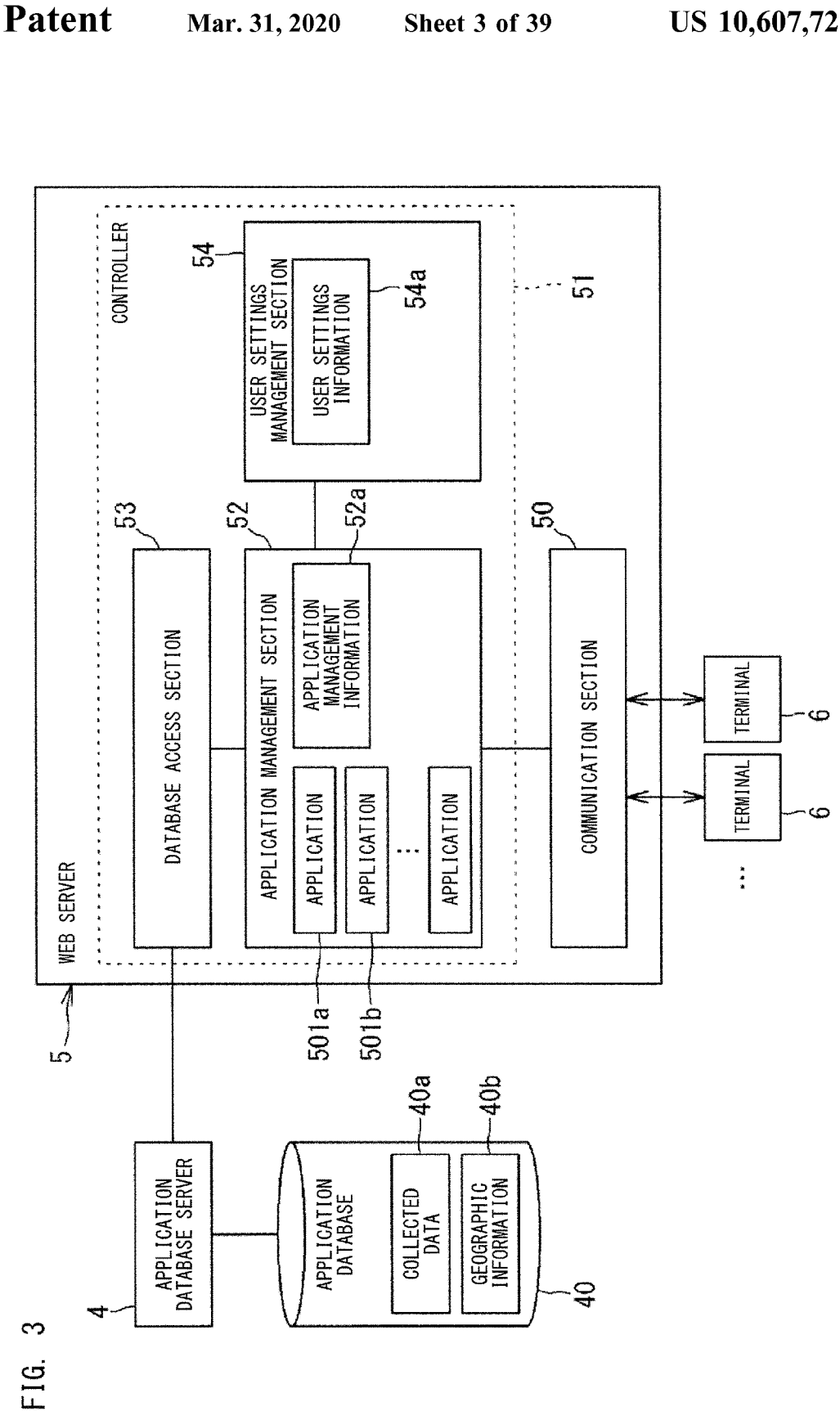
FIG. 3 is a configuration diagram of the Web server.

As shown in FIG. 3, the Web server 5 includes a communication section 50 and a controller 51. The Web server 5 is implemented by a computer having a memory and a processor. This also applies to the other servers 2, 3, and 4. The processor of the Web server 5 executes computer programs stored in the memory, to exhibit functions as the communication section 50 and the controller 51.

The communication section 50 communicates with one or a plurality of the terminals 6 via a computer network such as the Internet. The communication section 50 communicates with each terminal 6 in accordance with a communication protocol such as HTTP, for example. The controller 51 controls display of the terminal 6 via the communication section 50.

The controller 51 includes an application management section 52. The management section 52 includes a plurality of applications 501a, 501b, 501c, and 501d, and manages execution of these applications. The applications 501a, 501b, 501c, and 501d calculate indexes on the basis of the collected data 40a. The management section 52 also manages application configuration. The management section 52 can cause different applications to be displayed on the terminal 6 depending on the user. Accordingly, the management section 52 can cause different indexes to be displayed for each user. The management section 52 has application management information 52a for application management.

The controller 51 includes a user settings management section 54. The management section 54 sets a content to be displayed on the terminal 6 for each administrator being a user. The management section 54 has settings information 54a in which a display content is set for each administrator. The management section 54 can accept new creation and update of the settings information 54a, from an administrator being the user of the system 100.

Figure 4:
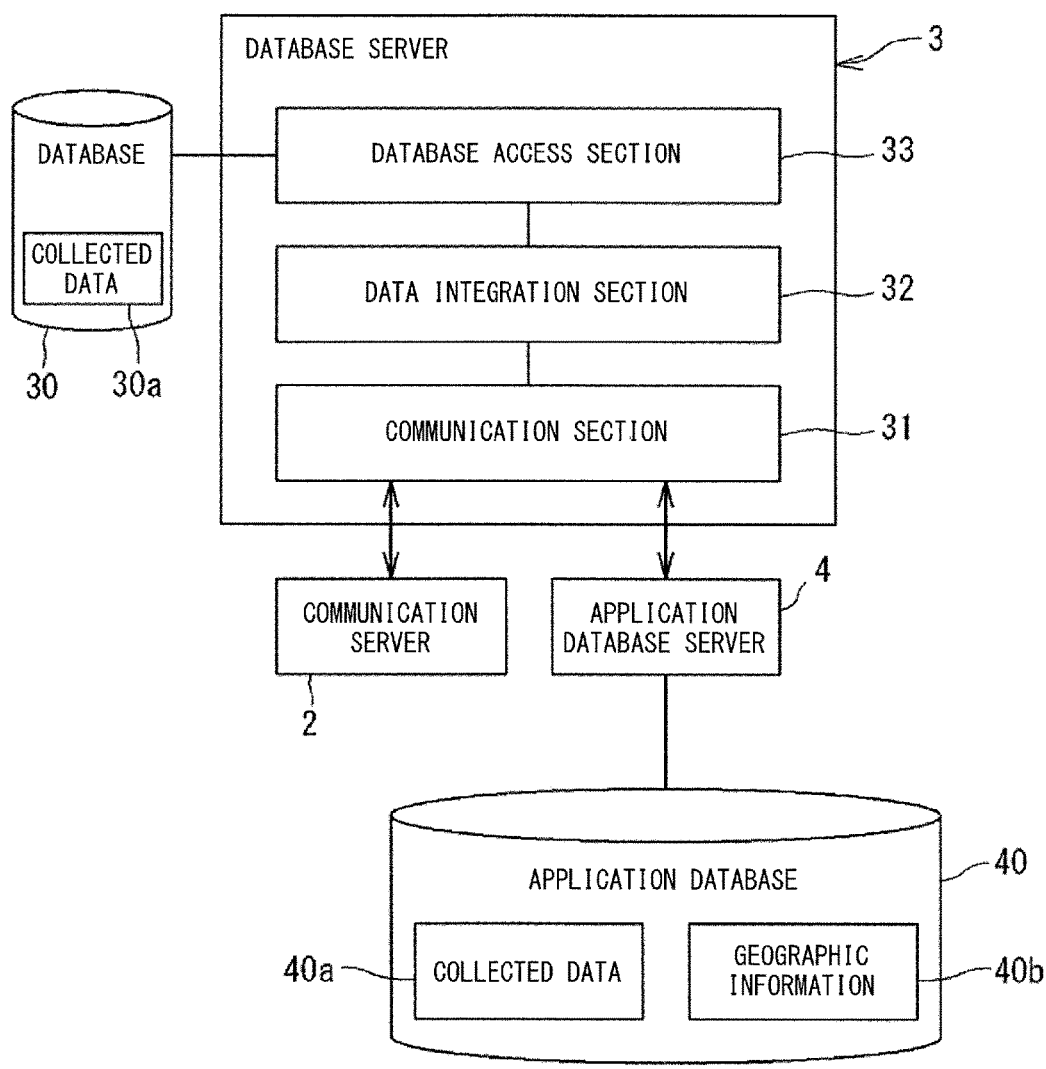
FIG. 4 is a configuration diagram of a database server.

As shown in FIG. 4, the database server 3 includes a communication section 31, a data integration section 32, and a database access section 33. The communication section 31 communicates with the application database server 4 and the communication server 2. The data integration section 32 integrates information collected from various kinds of information source 1 via the communication server 2, into data having a format accessible by the server 4. The integrated collected data 30a is stored in the database 30 via the database access section 33.

Figure 5:
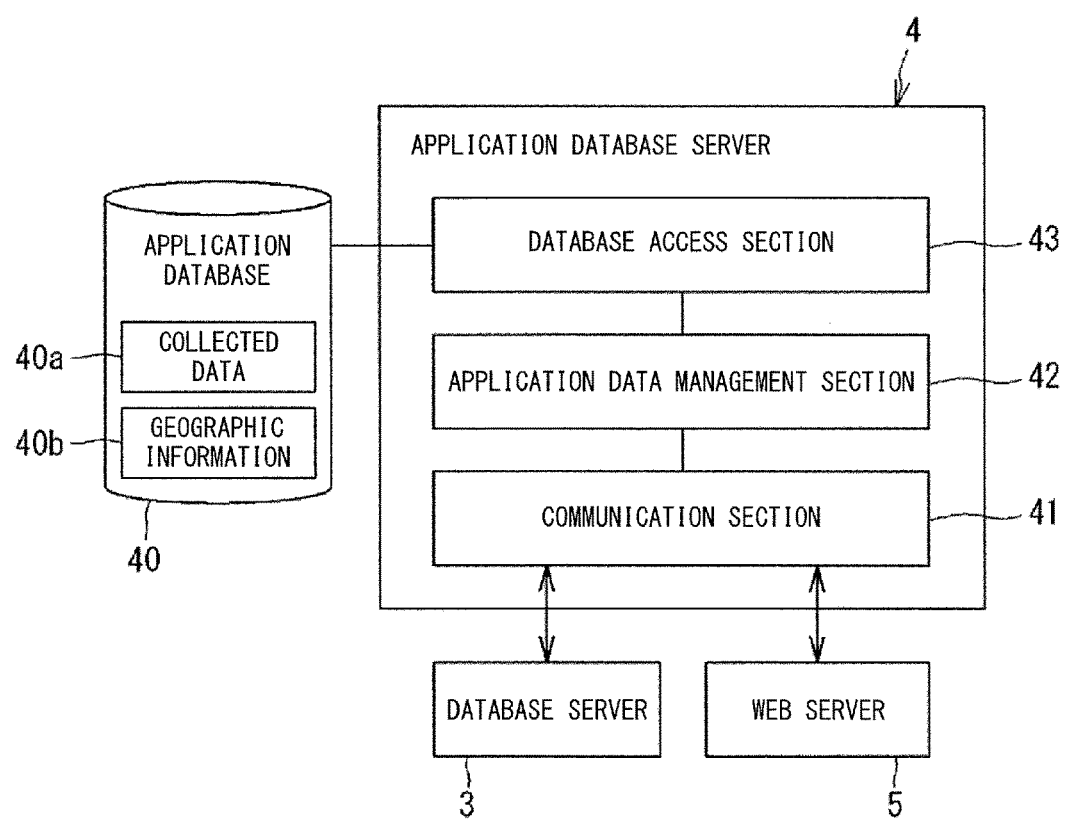
FIG. 5 is a configuration diagram of an application database server.

As shown in FIG. 5, the application database server 4 includes a communication section 41, an application data management section 42, and a database access section 43. The communication section 41 communicates with the database server 3 and the Web server 5. The application data management section 42 converts the collected data 30a stored in the database 30, so as to have a form appropriate for use by each application 501a, 501b, 501c, 501d in the Web server 5. The converted collected data 40a is stored in the database 40 via the database access section 43.

Figure 6:
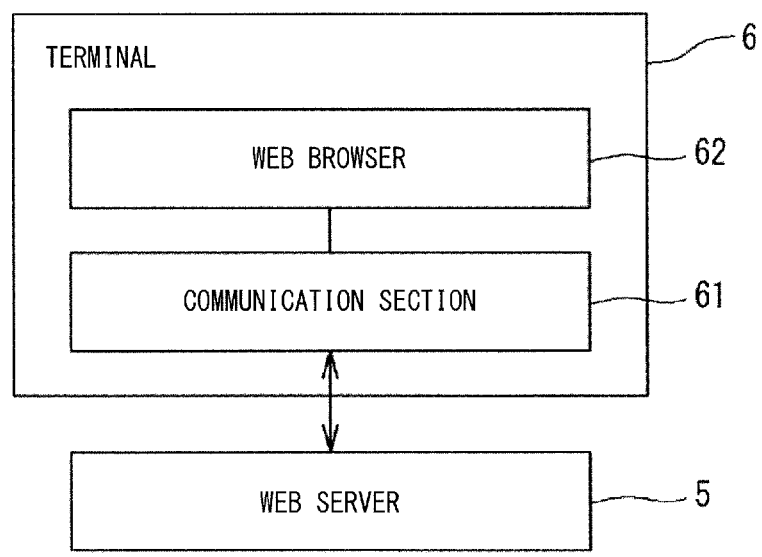
FIG. 6 is a configuration diagram of a terminal.

As shown in FIG. 6, the terminal 6 includes a communication section 61 and a Web browser 62. The terminal 6 is implemented by a computer having a memory and a processor. The terminal 6 is a PC, a tablet, or a smartphone, for example. Preferably, the terminal 6 is a mobile computer such as a tablet. Preferably, the terminal 6 has a touch panel as a display device. The processor of the terminal 6 executes computer programs stored in a memory to exhibit as functions as the communication section 61 and the Web browser 62.

The communication section 61 communicates with the Web server 5. The terminal 6 receives, by means of the Web browser 62, management information provided by the applications 501a, 501b, 501c, and 501d from the Web server 5.

Since the terminal 6 can access the server 5 through Web access, the terminal 6 can access the server 5 in a location-free manner.

Figure 7:
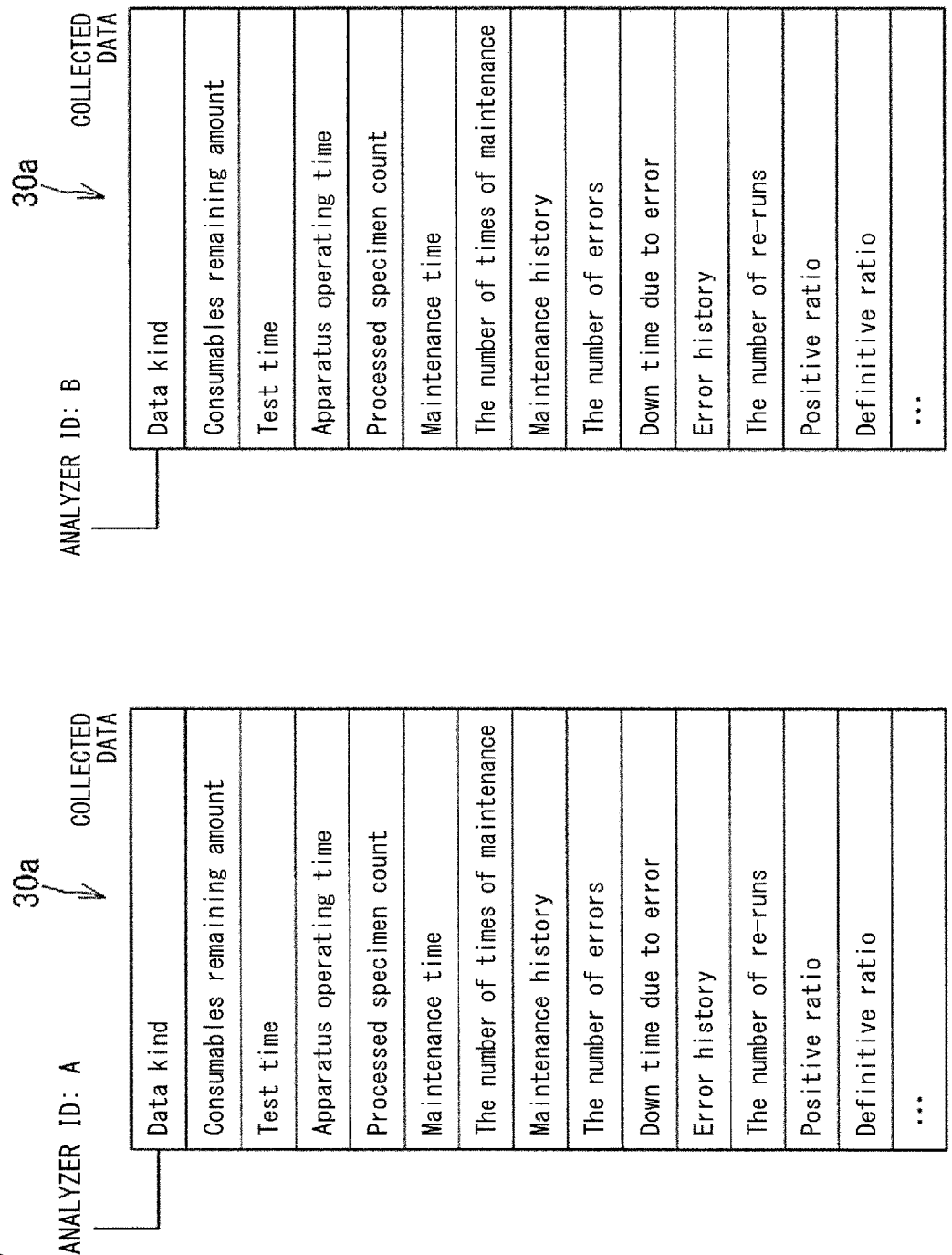
FIG. 7 is a data structure diagram of collected data.

FIG. 7 to FIG. 10 show examples of the collected data 30a stored in the database 30. The collected data 30a is stored in the database 30 for each kind (for each apparatus ID) of the information source 1. The collected data 30a shown in FIG. 7 is an example of data collected from each analyzer 10 which analyzes specimens. In the example shown in FIG. 7, the collected data 30a is stored for each ID of the analyzers 10 serving as the information source 1. FIG. 7 shows the collected data 30a collected from the analyzers 10 whose apparatus IDs are A and B. The data kinds of the collected data 30a from each apparatus 10 include, for example, consumables remaining amount, test time, apparatus operating time, processed specimen count, maintenance time, the number of times of maintenance, maintenance history, the number of errors, down time due to error, error history, the number of re-runs, positive ratio, definitive ratio, and the like.

Figure 8:
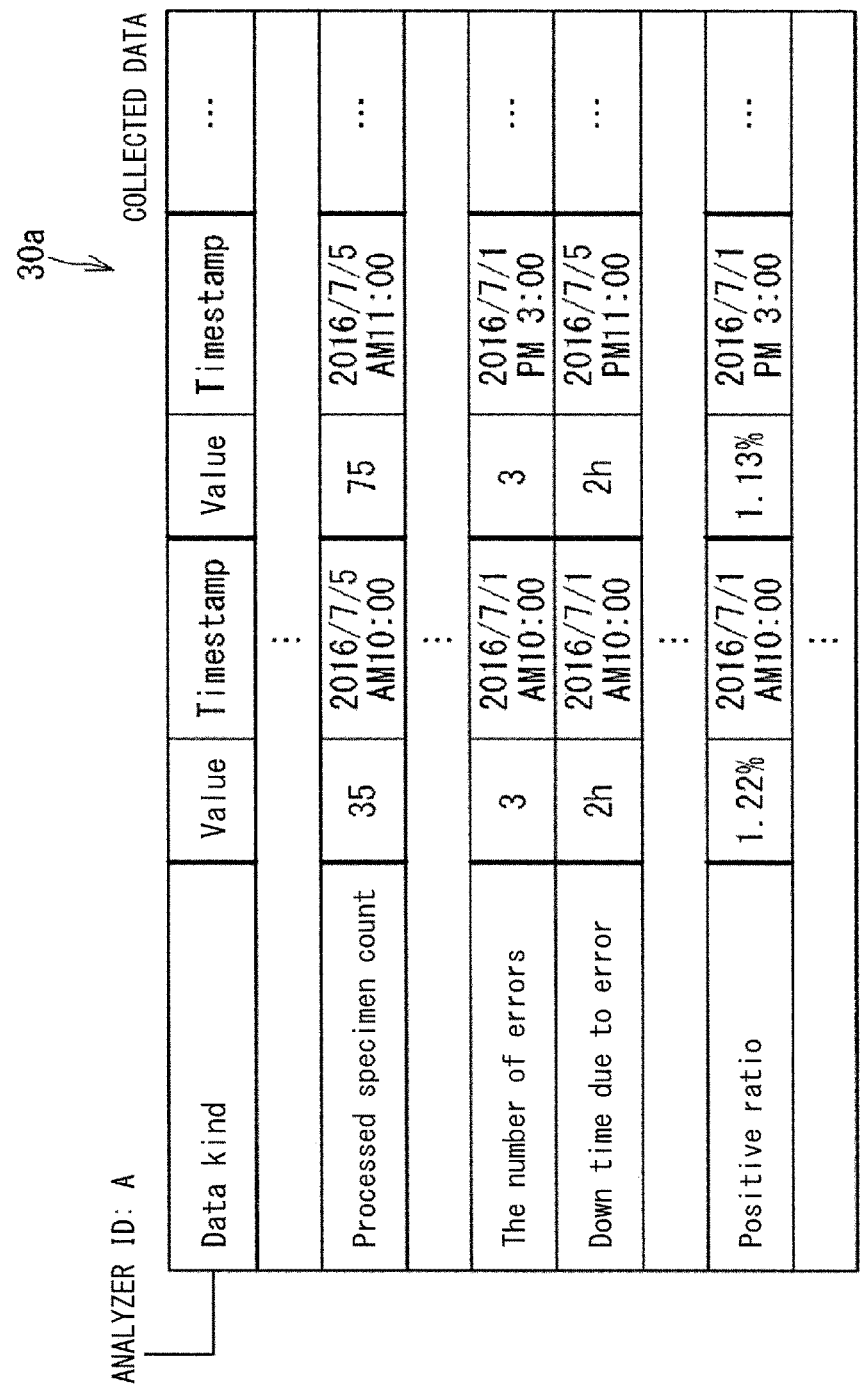
FIG. 8 is a data structure diagram of collected data.

FIG. 8 is another example of the collected data 30a. As shown in the example in FIG. 8, the collected data 30a may be stored as a time series log. For example, each piece of data is stored in the database 30 in association with a time stamp which indicates the time at which the piece of data was collected. For example, the number of processed specimens by a predetermined analyzer 10 (analyzer ID: A) is hourly obtained, and the time stamp that corresponds to the obtainment time and processed specimen count at that time are stored in the database 30. In this example, the value of processed specimen count increases with elapse of time. As the data kinds, the collected data 30a can include the number of errors, down time due to error, and positive ratio, for example, other than processed specimen count.

FIG. 9 is another example of the collected data 30a. The collected data 30a may be hierarchical data as shown in the example in FIG. 9. The hierarchical data is data shown in subdivision categories obtained by dividing a certain data kind from predetermined viewpoint. In the example shown in FIG. 9, each of the data kinds "processed specimen count" and "the number of re-runs" is subdivided into test items (for example, HGb-AG, HCV) for which each specimen was tested.

FIG. 10 is another example of the collected data 30a. The example shown in FIG. 10 is another example of the collected data 30a that is hierarchically structured. In the example shown in FIG. 10, the data kind ("the number of re-runs", "re-run ratio", etc.) relevant to abnormality of the analyzer 10 is subdivided in accordance with abnormality factors.

Figure 11:
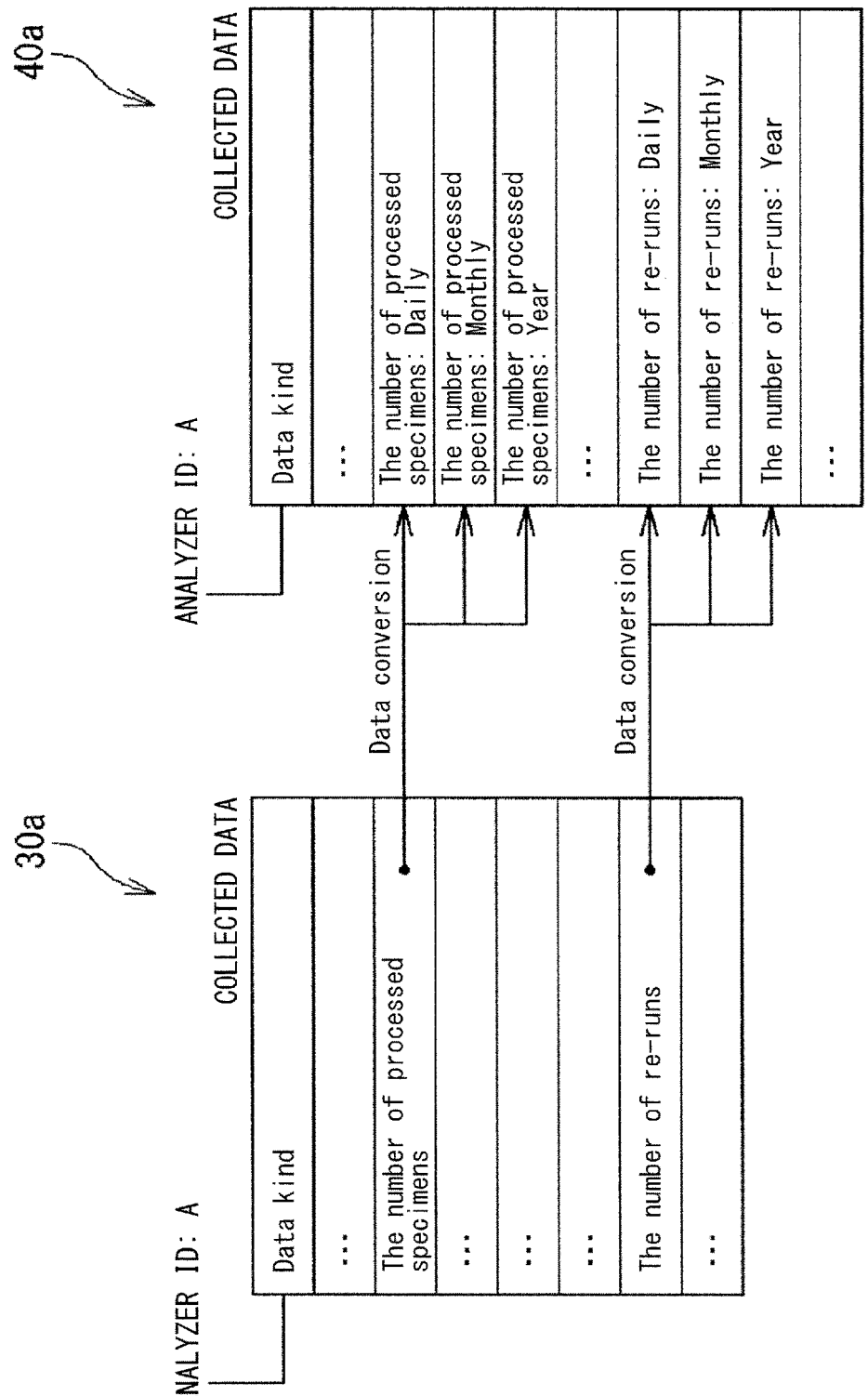
FIG. 11 is an explanatory diagram of conversion of collected data.

FIG. 11 and FIG. 12 each show conversion of the collected data 30a into the collected data 40a performed by the application database server 4. In the example shown in FIG. 11, on the basis of the time stamps stored in the collected data 30a, the application data management section 42 totals data for a predetermined data kind in each of the units of day, month, and year, and then stores the totaled data, as the collected data 40a, into the database 40. As a result of the conversion performed by the server 4, the collected data 40a is expressed in forms (for example, the number of processed specimens for each day, the number of processed specimens for each month, the number of processed specimens for each year) appropriate for display as indexes. As a result of the conversion performed by the server 4, an application for displaying an index corresponding to a data kind becomes able to display the index, by switching the unit among "day", "month", and "year".

In the example shown in FIG. 12, the application data management section 42 calculates data that corresponds to an index to be displayed by an application, from a plurality of data kinds in the collected data 30a. In the example shown in FIG. 12, from "apparatus operating time" and "down time due to error" of the analyzer 10 having the apparatus ID: A, the availability rate of the analyzer 10 is calculated. The availability rate is calculated by dividing the apparatus operating time by the sum of the apparatus operating time and the down time due to error. From "the number of processed specimens" and "the number of re-runs", the re-run ratio of the analyzer 10 is calculated. The re-run ratio is calculated by dividing the number of re-runs by the number of processed specimens.

The data converted by the application data management section 42 is stored, into the database 40, as the collected data 40a of each apparatus 10, 11, 12, 13, 14 (for each apparatus ID).

FIG. 13 and FIG. 14 show the geographic information 40b stored in the database 40. The geographic information 40b shows the areas in which the apparatuses 10, 11, 12, 13, and 14 serving as the information source 1 are installed. The geographic information 40b is used by an application in order to identify which area each apparatus 10, 11, 12, 13, 14 is installed in.

In the geographic information 40b, the areas are stored in a hierarchical manner, for example. In the geographic information 40b, the areas are stored in four hierarchies of, from widest, Area (1), Area (2), Area (3) and Area (4), for example. In FIG. 13, Area (1) indicates Japan; Area (2) indicates regions such as Kanto, Kinki, Tokai and Hokuriku, Hokkaido, and Tohoku; Area (3) indicates prefectures; and Area (4) indicates clinical laboratories. In FIG. 14, Area (1) indicates United States of America, Area (2) indicates states, Area (3) indicates cities, and Area (4) indicates clinical laboratories.

[2. Data Collection and Management Information Generation]

Figure 15:
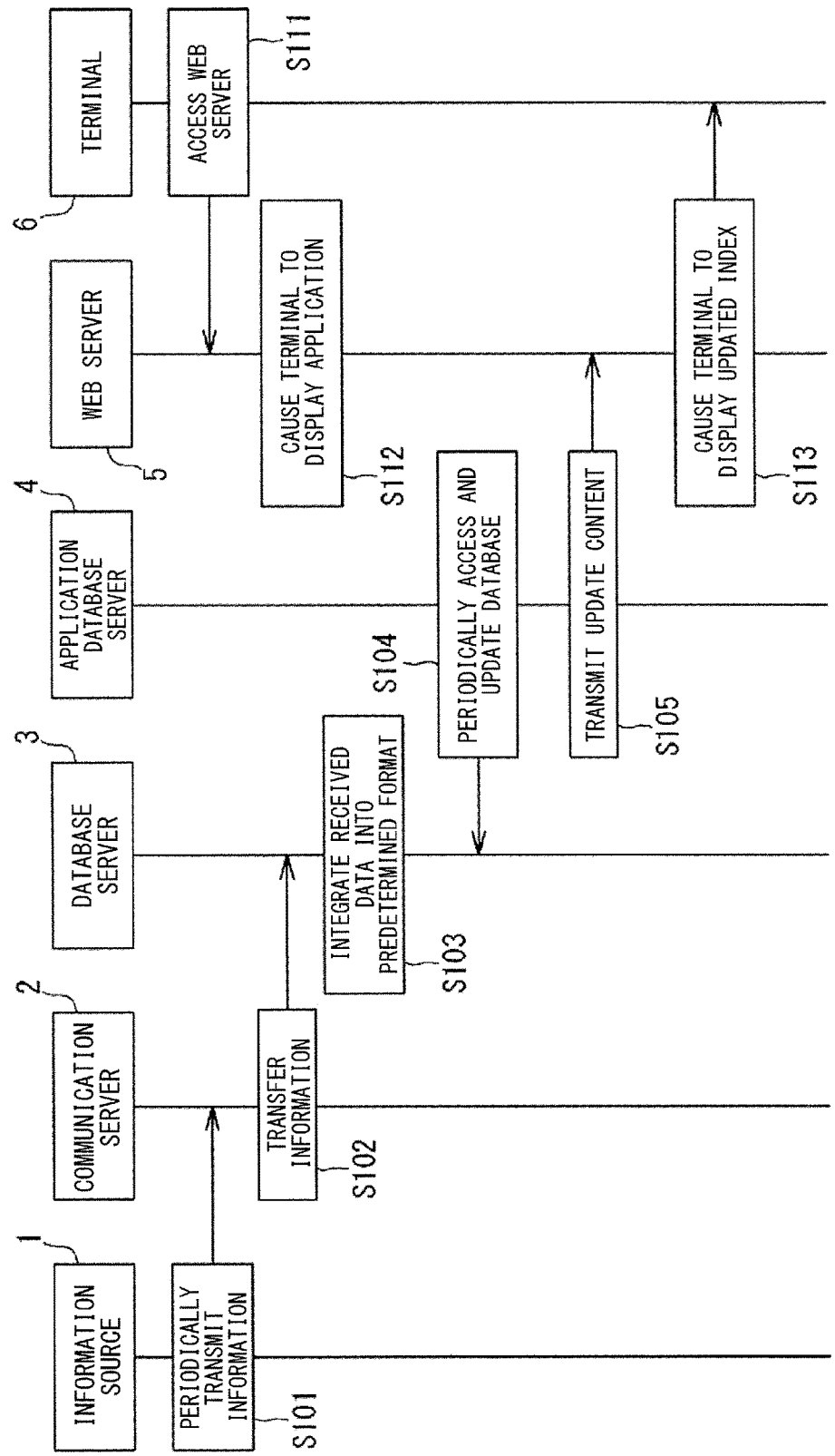
FIG. 15 is a sequence showing a procedure of data collection and management information display.

Collection of information from the information source 1 is performed in accordance with the procedure shown in FIG. 15, for example. In step S101, each apparatus 10, 11, 12, 13, 14 serving as the information source 1 periodically transmits, to the communication server 2, information or the like regarding the operation status of the clinical laboratory or the operation status of the analyzer.

In step S102, the communication server 2 transfers, to the database server 3, the information received from the information source 1. In step S103, the server 3 converts the transferred information into a uniform format, and then stores, into the database 30, the data having the uniform format as the collected data 30a for each apparatus installed in its corresponding place.

In step S104, the application database server 4 periodically accesses the database 30. The server 4 generates the collected data 40a which is data converted from the collected data 30a stored in the database 30. The server 4 updates the database 40, with the generated collected data 40a. In step S105, the Web server 5 periodically accesses the database 40 which manages, in a centralized manner, the collected data 40a based on the information collected from the information source 1, whereby the Web server 5 refers to the database 40. When being accessed by the Web server 5, the server 4 transmits, to the Web server 5, the collected data 40a being an update content of the database 40. Each application 501a, 501b, 501b, 501c, 501d of the Web server 5 calculates an index or the like for clinical laboratory management, on the basis of the collected data 40a transmitted from the database 40.

As shown in step S111, when necessary, the administrator of the clinical laboratory operates the terminal 6 to access the Web server 5, thereby being able to log in. In step S112, the server 5 generates the display screen 500 (see FIG. 1) including a plurality of applications 501a, 501b, 501c, and 501d, and causes the terminal 6 having accessed the server 5 to display the display screen 500 of the management information. On the display screen 500 (the dashboard 500a), the applications 501a, 501b, 501c, and 501d displays values of indexes calculated on the basis of the collected data 40a. In step S113, when the content of the database 40 is updated in accordance with change in the status of the clinical laboratory, the application 501a, 501b, 501c, 501d accordingly and automatically updates the display (index value, etc.), of the terminal 6, that corresponds to at least one of indexes displayed on the display screen 500.

Figure 16A:
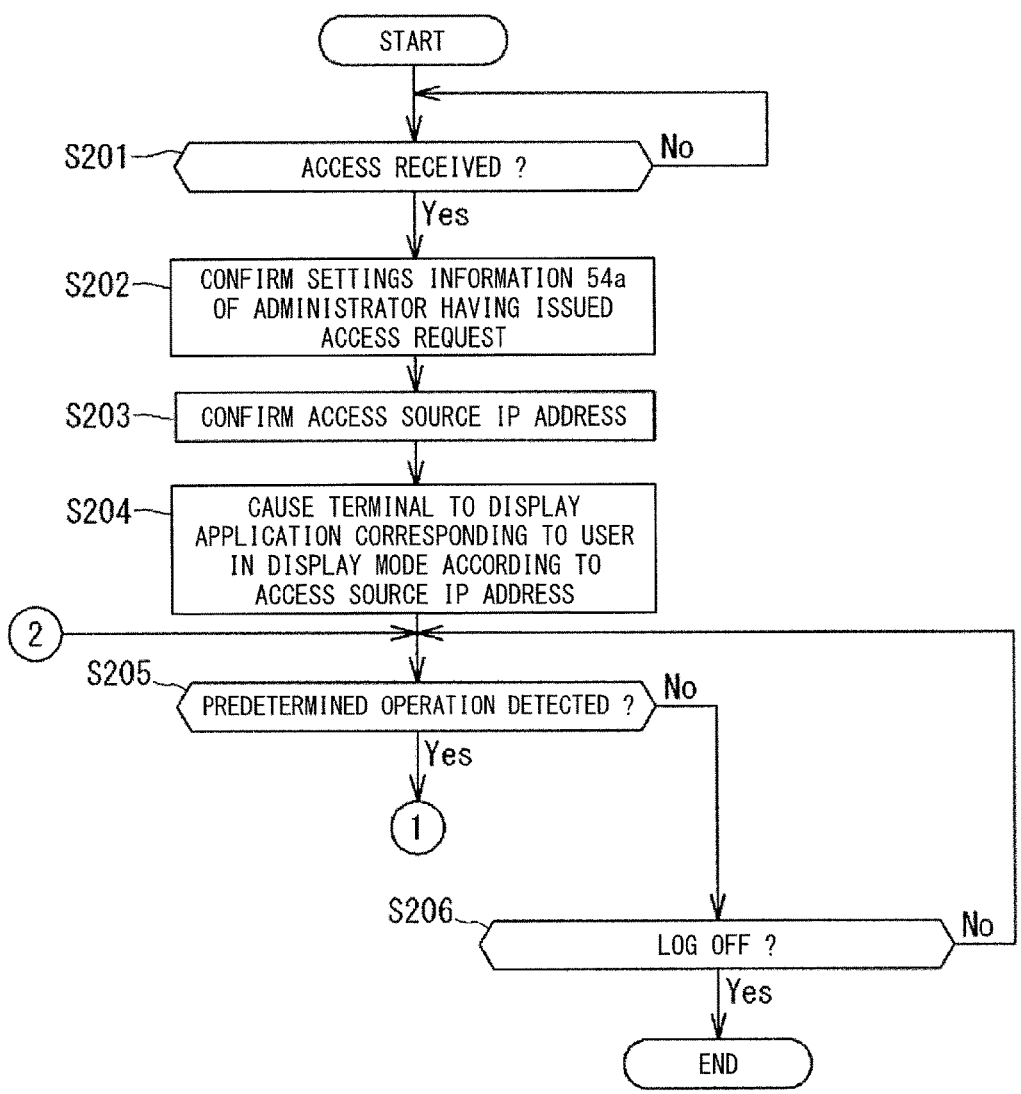
FIG. 16A is a flow chart showing a procedure of display control performed by a Web server.
Figure 16B:
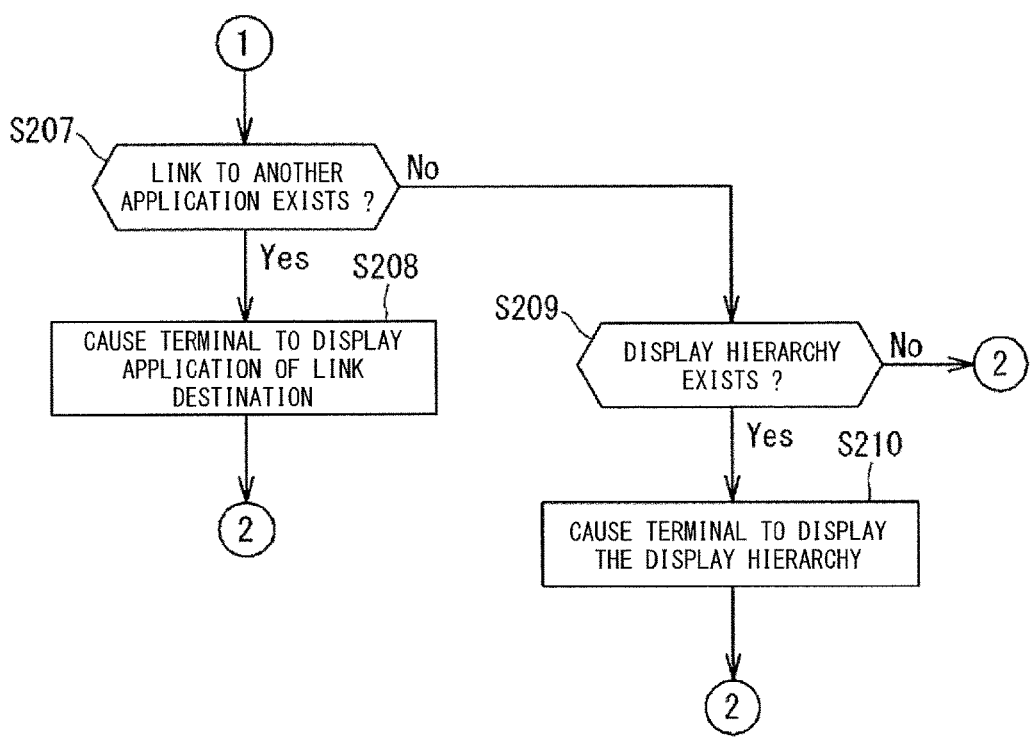
FIG. 16B is a flow chart showing a procedure of display control performed by the Web server.

FIG. 16A and FIG. 16B show the procedure of display control regarding the terminal 6 of which access has been received by the server 5. The server 5 receives an access request from the terminal 6 in step S201. The access request includes authentication information such as a user ID and a password of an administrator. On the basis of the authentication information, the server 5 performs authentication of the administrator being the user. If the authentication has succeeded, the server 5 permits log-in of the administrator.

The access request may include an IP address of a network device (access source) via which the terminal 6 has established Internet connection. The IP address serves as information regarding the location of the terminal 6. The IP address allows ascertainment of the location of the terminal 6. The information regarding the location of the terminal 6 can be discerned by the Web server 5, for example, between a case where the terminal 6 of the administrator has established connection with the Web server 5 via a LAN in the workplace of the administrator or in the clinical laboratory, and a case where the terminal 6 of the administrator has established connection with the Web server 5 via a mobile communication network or a public wireless LAN when the administrator is out of the workplace.

When a user log-in has been made on the basis of the access request, the controller 51 confirms, in step S202, the user settings information 54a of the administrator who has issued the access request. On the basis of the settings information 54a (see FIG. 3), the controller 51 selects an application to be provided to the administrator being the user. The selection of the application is also a selection of an index to be displayed by the application. In step S203, the controller 51 confirms the access source IP address included in the access request.

In step S204, the controller 51 generates the display screen 500 (see FIG. 1) in which the applications 501a, 501b, 501c, and 501d selected on the basis of the settings information 54a are arranged in the dashboard 500a, and causes the terminal 6 of the user logging in, to display the display screen 500. The application 501a, 501b, 501c, 501d displayed in a form of an icon indicates the value of the index in the form of a numerical value. The application 501a, 501b, 501c, 501d displayed in a form of an icon may indicate the value of the index in the form of a graph. With respect to the display screen 500, the display mode of each index or the like is determined on the basis of the access source IP address (information regarding the location of the terminal), and the index or the like is displayed in the determined display mode. This will be described later.

When a user operation such as clicking or tapping is made on the displayed application 501a, 501b, 501c, 501d, the display content of the display region 500a is switched. For example, in step S205, it is assumed that a user operation such as clicking or tapping has been detected in the dashboard 500a shown in FIG. 1. In this case, in step S207 shown in FIG. 16B, it is determined whether or not the user operation has been made in a region for which a link to another application has been set. When the operation has been made in a region for which a link to another application has been set, an application 500 being the link destination is displayed on the display region 500a of the terminal 6. In step S209, it is determined whether the user operation has been made in a region for which a display hierarchy has been set. When there is a display hierarchy, the set display hierarchy is displayed in the display region 500. Display of another r application and a display hierarchy will be described later. In step S206, when a log-off operation is performed, the process ends.

FIG. 17A, FIG. 17B, FIG. 17C, and FIG. 17D show examples of the settings information 54a. In the example shown in FIG. 17A, the settings information 54a includes users, one or a plurality of applications associated with each user, and display settings associated with each application. In the example shown in FIG. 17A, for example, the user having the user ID of a001 is associated with a plurality of applications including applications whose application IDs are "A1", "A2", and "A3". In the settings information 54a, applications associated with a user are displayed on the dashboard 500a for that user. For example, in the dashboard 500a shown in FIG. 1, four applications (widgets) 501a, 501b, 501c, and 501d are displayed. These applications 501a, 501b, 501c, and 501d are associated, in the settings information 54a, with the user to be provided with the dashboard 500a shown in FIG. 1.

Figure 17A:
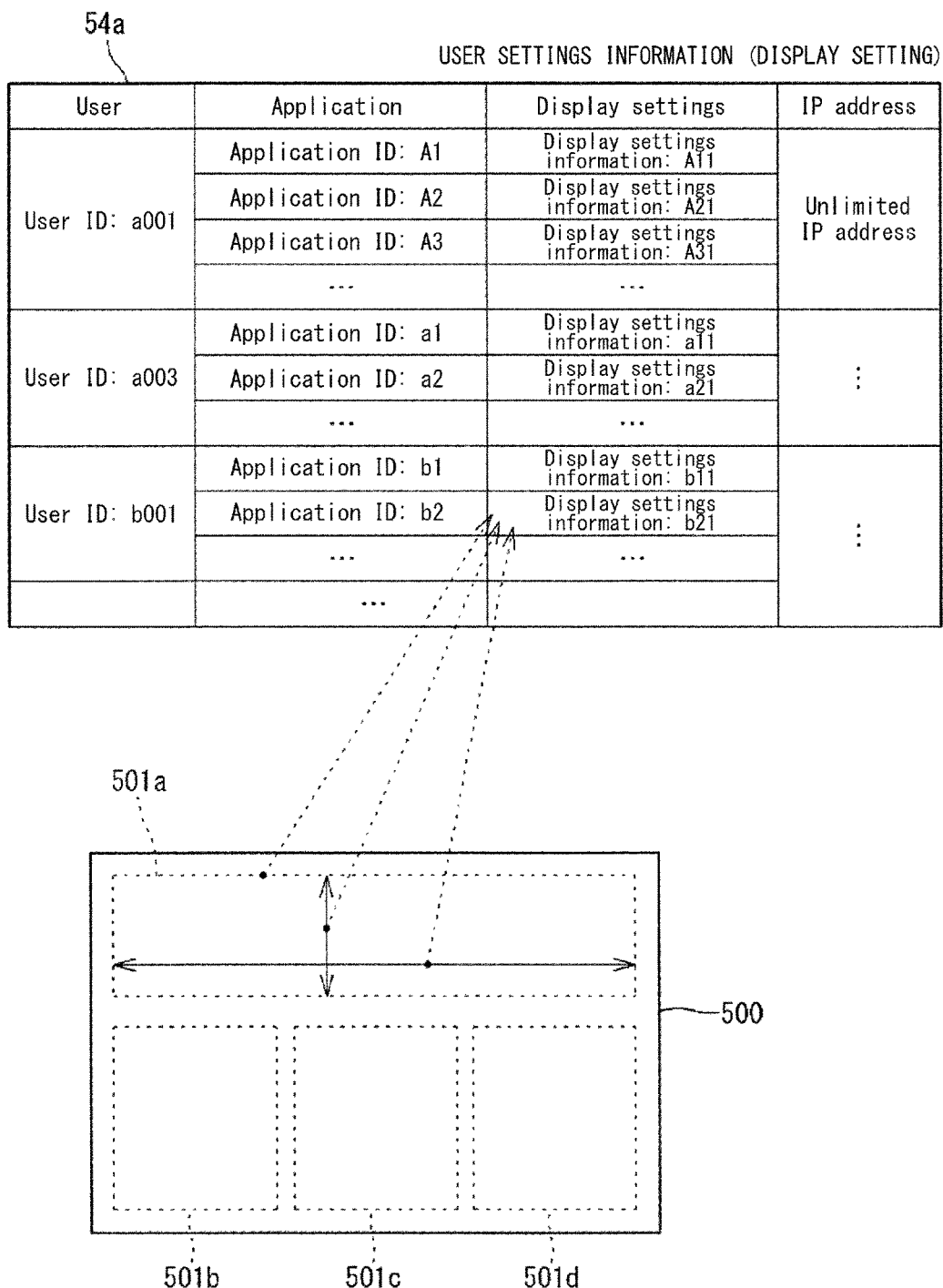
FIG. 17A is a data structure diagram of settings-information.

The display settings shown in FIG. 17A include display settings information, such as display position, size, and the like, to be used when each application is displayed in the dashboard 500a. The display settings information may include information regarding the display mode according to the access source IP address. The controller 51 generates the dashboard 500a which displays each application associated with the user in the settings information 54a, in accordance with the display settings associated with the application in the settings information 54a.

The controller 51 may obtain from the terminal 6 information indicating the screen size of the terminal 6, and may automatically adjust the arrangement of the applications (indexes) to be displayed on the terminal 6 and the display sizes of the indexes included in the applications, in accordance with the screen size of the terminal 6. The settings information 54a shown in FIG. 17A may include information indicating the user kind which indicates, for example, whether the user is an administrator of a clinical laboratory, a laboratory technician, or a person in charge on the system providing side. The user kind can be freely selected and set by the user. The controller 51 can cause different contents of the screen to be displayed on the terminal 5, in accordance with the user kind.

The settings information 54a shown in FIG. 17A has an IP address set for each user. The IP address indicates an access source IP address without display limitation (unlimited IP address) As the unlimited IP address in the settings information 54a, an IP address is set of a network device in the clinical laboratory managed by the administrator being the user or in the workplace of the administrator.

In the example shown in FIG. 17B, the settings information 54a includes user's roles, one or a plurality of applications associated with each user's role, and display settings associated with each application. Also the settings information 54a shown in FIG. 17B can include an IP address for each user. The settings information 54a shown in FIG. 17B does not have information of individual users, and applications and display settings are associated with each user's role. The user's roles are "multi-site management", "single site management", and "clinical laboratory operation", for example. The settings information 54a shown in FIG. 17B is used together with the settings information 54a shown in FIG. 17C. In the settings information 54a shown in FIG. 17C, the user's role is set for each user.

The settings information 54a shown in FIG. 17A is appropriate for a case where the applications to be displayed and display settings are finely customized for each user. On the other hand, the settings information 54a shown in each of FIG. 17B and FIG. 17C is appropriate for a case where it is desired to set applications and display settings suitable for the role of each user by simply setting a user' role for each user. For example, in a case where a new user starts using the management system 100, the user simply sets the user's role as in the settings information 54a shown in FIG. 17C, and the user need not make detailed settings as shown in FIG. 17A. On the basis of the set role, the controller 51 refers to the settings information 54a shown in FIG. 17B, thereby being able to ascertain the applications to be displayed and display settings. With respect to the settings information 54a shown in FIG. 17A, when the user has set indexes so as to be displayed in accordance with the user's taste, the set contents are registered as the settings information 54a as shown in FIG. 17A.

The value of the index calculated by each application 501a, 501b, 501c, 501d displayed in the dashboard 500a is calculated from the collected data 40a regarding the apparatus 10, 11, 12, 13, 14 which the user is in charge of. FIG. 18 shows the user settings information 54a in which users are associated with the areas and apparatuses of which the users are in charge.

In the settings information 54a shown in FIG. 18, the areas are managed in a hierarchical manner. On the basis of the settings information 54a shown in FIG. 18, each application can ascertain the areas and analyzers which the user is in charge of, and each application can calculate the index value for the user.

With reference to the settings information 54a above, each application calculates an index on the basis of the collected data 40a regarding the apparatus 10, 11, 12, 13, 14 of which management the user is in charge of. For example, if the user is in charge of management of a plurality of clinical laboratories, an index is calculated from the collected data 40a from the apparatuses 10, 11, 12, and 13 in the plurality of clinical laboratories which the user is in charge of. If the user is in charge of management of only one clinical laboratory, an index is calculated from the collected data 40a from the apparatuses 10, 11, 12, and 13 in the single clinical laboratory. If an administrator is in charge of the Kanto region in Japan, an index is calculated from the collected data 40a from the clinical laboratories in the Kanto regions. If another administrator is in charge of the United States, an index is calculated from the collected data 40a from the clinical laboratories in the United States.

In step S204 described above, each application 501a, 501b, 501c, 501d causes the calculated index to be displayed in the dashboard 500a of the terminal 6 as shown in FIG. 1. It should be noted that the dashboard 500a shown in FIG. 1 is for multi-site administrator, and thus, indexes calculated from the collected data 40a from multi sites are displayed.

Figure 19:
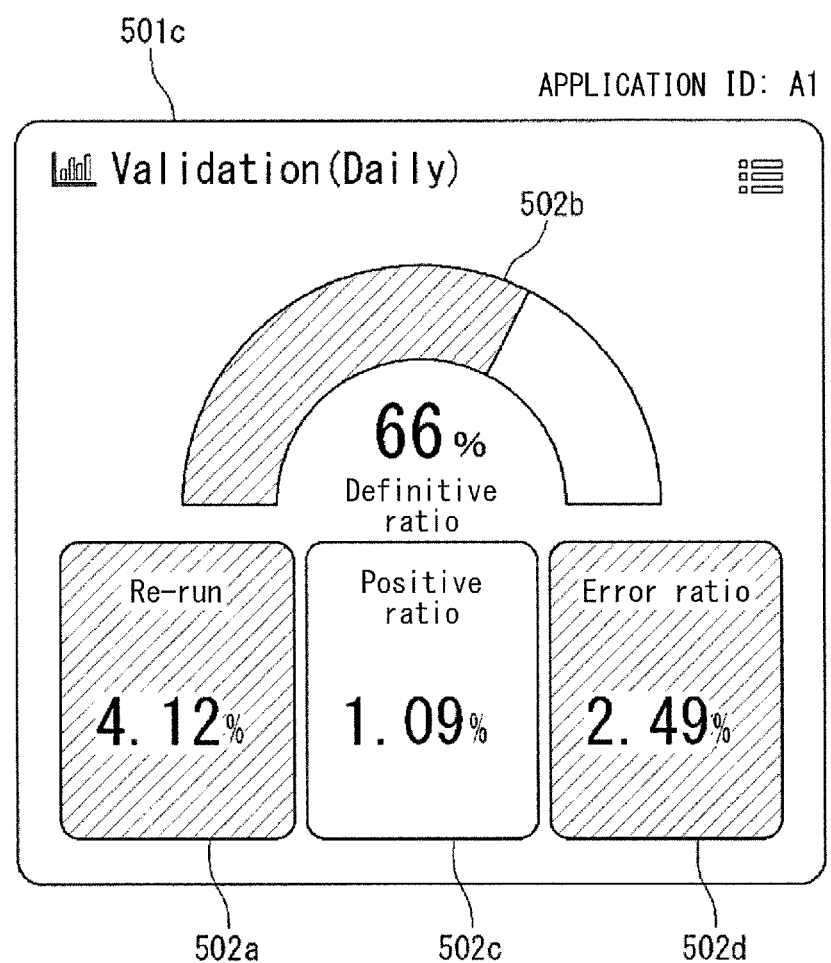
FIG. 19 is a display screen realized by an application.

FIG. 19 shows the application 501c shown in FIG. 1. The application 501c is an application which displays an index regarding Validation, and can display four indexes, i.e., "re-run ratio" 502a, "definitive ratio" 502b, "positive ratio" 502c, and "error ratio" 502d. These four index values are values calculated from the collected data 40a from multi sites which the user is in charge of. These four indexes are indexes that indicate specimen analysis statuses by the analyzers. The re-run ratio 502a and the like are also indexes that indicate the abnormality occurrence status of the analyzers.

The application as shown in FIG. 19 is managed by the application management section 52 of the controller 51, on the basis of the application management information 52a set for each application. If the application 501c shown in FIG. 19 has an application ID "A1", the application management information 52a of the application 501c shown in FIG. 19 has a structure shown in FIG. 20, for example. The other applications 501a, 501b, and 501d are also managed in accordance with the management information 52a.

The management information 52a shown in FIG. 20 includes an index to be displayed by the application 501c, a link destination, and a display hierarchy. The index to be displayed is an index to be displayed in the dashboard 500a by the application 501c. In FIG. 20, as the index to be displayed, four indexes are set, i.e., "re-run ratio" 502a, "definitive ratio" 502b, "positive ratio" 502c, and "error ratio" 502d.

The link destination shown in FIG. 20 indicates another application associated with the application 501c or the indexes 502a, 502b, 502c, and 502d displayed in the application 501c. As the display hierarchy shown in FIG. 20, Null is set. The display hierarchy will be described later.

When the index 502a, 502b, 502c, 502d displayed in the dashboard 500a is selected through a user operation such as clicking or tapping, the controller 51 causes the application set in the link destination to be displayed in the display region 500a as shown in FIG. 21, instead of the dashboard shown in FIG. 1.

Here, in FIG. 20, for all the indexes 502a, 502b, 502c, and 502d, an application having an application ID "B1" is set as the link destination. Therefore, when any of the indexes in the application 501c shown in FIG. 19 is selected, the application having the application ID "B1" is displayed in the display region 500a as shown in FIG. 21. Here, when the application 501c is selected, the screen is switched to the screen shown in FIG. 21. Thus, selection of the application 501c can also be regarded as selection of all the plurality of indexes 502a, 502b, 502c, and 502d.

In FIG. 20, for all the indexes 502a, 502b, 502c, and 502d in the application 501c, the same application (B1) is set as the link destination. However, a different link destination may be set for each index. When a different link destination is set for each index, the application to be displayed in the display region 500a is different depending on the index that is selected.

The application (ID: B1) shown in FIG. 21 is an application regarding the operation status of the clinical laboratories. The application shown in FIG. 21 displays, as the indexes for clinical laboratory management, "the number of specimens" 502e, "the number of re-runs" 502f, "re-run ratio" 502a, "positive ratio" 502c, "definitive ratio" 502b, "error" 502d, "cost" 502g, and "system availability" 502h. These index include the indexes 502a, 502b, 502c, and 502d displayed by the application 501c in FIG. 19, and other indexes 502e, 502f, 502g, and 502h (relevant indexes) relevant to the indexes 502a, 502b, 502c, and 502d. Thus, the application (ID: B1) shown in FIG. 21 displays the indexes selected in the dashboard 500a, and relevant indexes. The relevant indexes are indexes that are different from the indexes selected in the dashboard 500a, but through the display of the relevant indexes, the administrator can obtain more information of indexes. For example, in the row "Saitama" shown in FIG. 21, the values of two indexes of the number of re-runs 502f and the re-run ratio 502a are bad, but the system availability 502h is 92% and a high state thereof is maintained. Therefore, the user who has referred to the screen shown in FIG. 21 can ascertain that the analyzers are not in abnormal states, but that the number of re-runs has increased. Further, from the fact that the number of re-runs has increased nonetheless the apparatuses are not in abnormal states, the user can infer that the factor of the re-runs is not worsened states of analyzers but abnormality of specimens or abnormality of reagents.

The application (ID: B1) shown in FIG. 21 displays, on the display screen 500a, each index 502a, 502b, 502c, 502d, 502e, 502f, 502g, 502h so as to be divided in a plurality of categories. In FIG. 21, the plurality of categories are categories corresponding to regions which the user is in charge of. In FIG. 21, the value of each index 502a, 502b, 502c, 502d, 502e, 502f, 502g, 502h is displayed so as to be divided in categories 503 corresponding to the regions: Hokkaido, Tohoku, Saitama, Tokyo, Tokai and Hokuriku, Kinki, Chugoku and Shikoku, and Kyushu. For example, the categories 503 are determined with reference to the regions that are set as the area which the user is in charge of in the user settings information 54a shown in FIG. 18. The area which the user is in charge of can be set as the settings information 54a. Thus, the categories 503 can be set for each user. For example, in a case where a user whose area in charge is the United States, the indexes are displayed so as to be divided in categories corresponding to the states or cities in the United States.

Here, it is assumed that the administrator who uses the screens shown in FIGS. 1, 19, and 21 is in charge of Japan as the management area. According to the application 501c shown in FIG. 1 and FIG. 19, each index value is displayed as a composite index value of statuses of many clinical laboratories included in a first region, i.e., Japan. Therefore, by referring to the dashboard shown in FIG. 1, the administrator can ascertain the status of the entirety of the management area in charge.

Meanwhile, according to the application (ID: B1) shown in FIG. 21, each of the indexes including the indexes 502a, 502b, 502c, and 502d selected in the dashboard 500a is displayed so as to be divided in the categories 503 corresponding to a plurality of second regions (Hokkaido, etc.) included in Japan. The values of the indexes corresponding to the regions are calculated on the basis of the apparatuses 10, 11, 12, 13, and 14 installed in the corresponding regions. Thus, by referring to the application shown in FIG. 21, the administrator can ascertain the index for each region being a subdivision of the management area in charge. The display divided for each region is given not only for the indexes selected in the dashboard 500a, but also for relevant indexes. Thus, the administrator can ascertain more detailed statuses of the clinical laboratories.

For example, by referring to the application 501c in the dashboard shown in FIG. 1, the administrator can ascertain that the re-run ratio 501a and the error ratio 502d in the entirety of the management area in charge have worsened. In that case, the administrator selects the application 501c by clicking, tapping, or the like, to cause the application (ID: B1) shown in FIG. 21 to be displayed, thereby being able to ascertain that the worsening of the re-run ratio 502a is occurring in "Saitama" and "Tokyo" in particular, and worsening of the error ratio 502d is occurring in "Tokyo" and "Tokai and Hokuriku" in particular. Accordingly, the administrator can easily take appropriate measures for these regions.

It should be noted that if another of the applications 501a, 501b, and 501c or an index in the applications 501a, 501b, and 501c in the dashboard shown in FIG. 1 is selected, an application being the link destination of the selected application or index is displayed in the display region 500a.

The application (ID: B1) shown in FIG. 21 is managed according to the application management information 52a shown in FIG. 22, by the application management section 52. The management information 52a shown in FIG. 22 includes an index to be displayed by the application (ID: B1) shown in FIG. 21, a link destination, and a display hierarchy. The index to be displayed is an index to be displayed in the display region 500a by the application shown in FIG. 21. In FIG. 22, as the index to be displayed, eight indexes are set, i.e., "re-run ratio" "the number of re-runs", "definitive ratio", "positive ratio", "error ratio", "processed specimen count", "cost", and "system availability".

As the link destination shown in FIG. 22, Null is set. That is, there is no application that is associated with the application (ID: B1) shown in FIG. 21. Therefore, even if a selection operation is performed in the display region 500a shown in FIG. 21, the display region 500a is not switched to another application. It should be noted that switching of the display of the display region 500a can be performed through operation made onto the display region 500b, 500c.

As the display hierarchy shown in FIG. 22, the two indexes "re-run ratio" and "re-run ratio" are allocated with a first hierarchical rank and a second hierarchical rank, respectively. The other indexes "definitive ratio", "positive ratio", "error ratio", "processed specimen count", "cost", and "system availability" are each allocated with only the first hierarchical rank.

Figure 24:
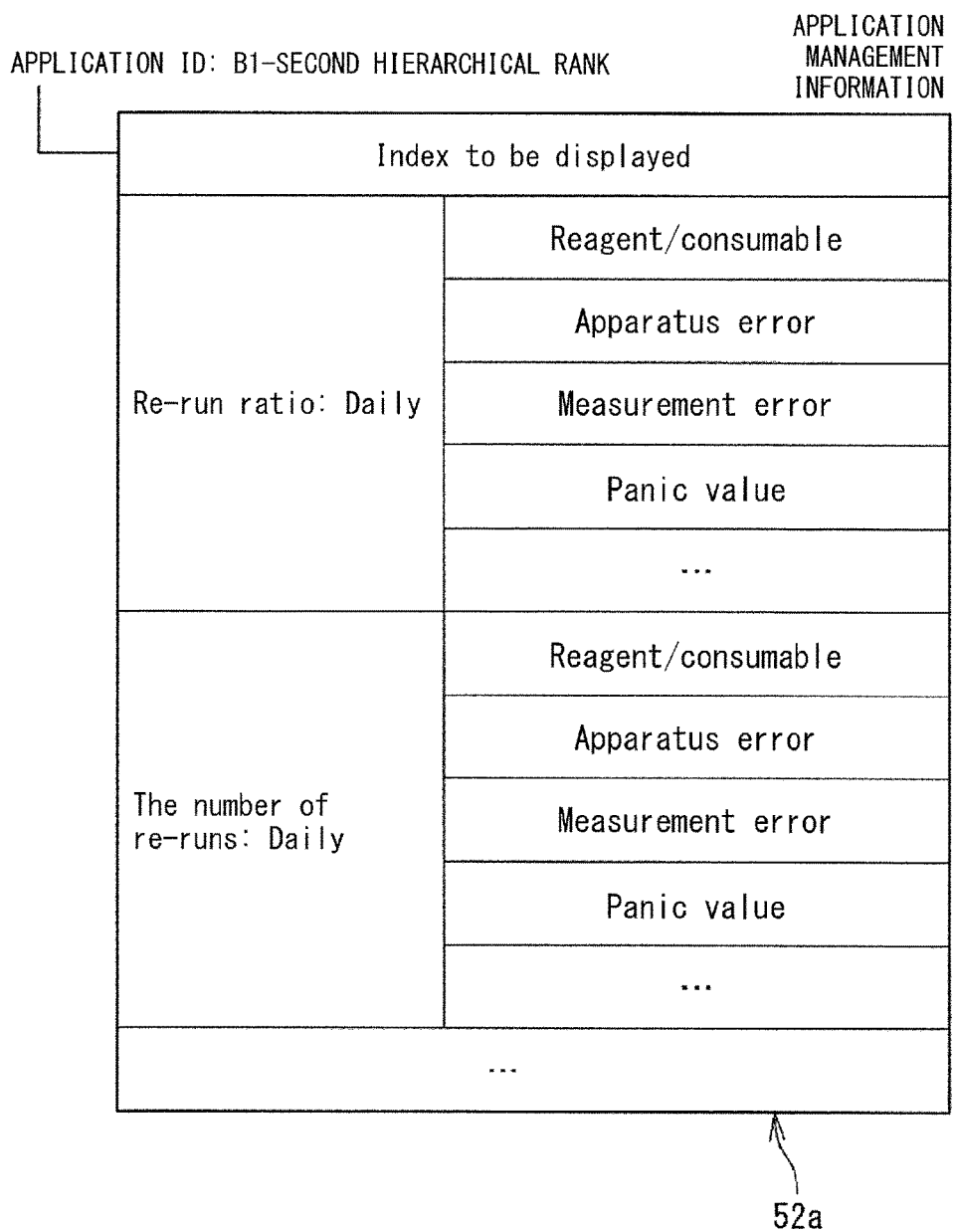
FIG. 24 is a data structure diagram of the application management information.

The display hierarchy is a hierarchy for displaying the indexes 502a, 502b, 502c, 502d, 502f, 502g, and 502h in more detailed categories, than in a normal display mode such as in FIG. 21. In the first hierarchical rank, categories corresponding to a plurality of test items for tests executed by the analyzers 10 are set as shown in FIG. 23. In the second hierarchical rank, categories corresponding to abnormality factors in the analyzers 10 are set as shown in FIG. 24.

In the embodiment, the display hierarchy is used so that, when any one of the categories 503 corresponding to the regions shown in FIG. 21 is selected through a user operation, each index 502a, 502b, 502c, 502d, 502e, 502f, 502g, 502h in the selected region is displayed so as to be divided in predetermined categories (categories corresponding to test items or categories corresponding to abnormality factors).

For example, when a user operation of selecting the row "Hokkaido" is performed in FIG. 21, the application (ID: B1) shown in FIG. 21 keeps the display of the index values in Hokkaido and further displays the value of each index in Hokkaido so as to be divided in categories 505 corresponding to the test items, as shown in FIG. 25. FIG. 25 is a display based on the first hierarchical rank shown in FIG. 23. In the present embodiment, as the initial setting, the first hierarchical rank which is displayed in the categories corresponding to test items is selected. It should be noted that the first hierarchical rank can be displayed through an operation of selecting a "By item" button 504 in the display region 500a, as shown in FIG. 25.

The application (ID: B1) calculates the value of each index 502a, 502b, 502c, 502d, 502f, 502g, 502h, for each test item set in FIG. 23. In FIG. 25, the test items include "Tp", "HBs-Ag", "HBs-Ab", "HCV", "HTLV", "HIV", and "B19". By referring to the screen shown in FIG. 25, the administrator can ascertain, for each test item, the indexes, 502a, 502b, 502c, 502d, 502f, 502g, and 502h indicating the operation status of the analyzers.

Figure 26:
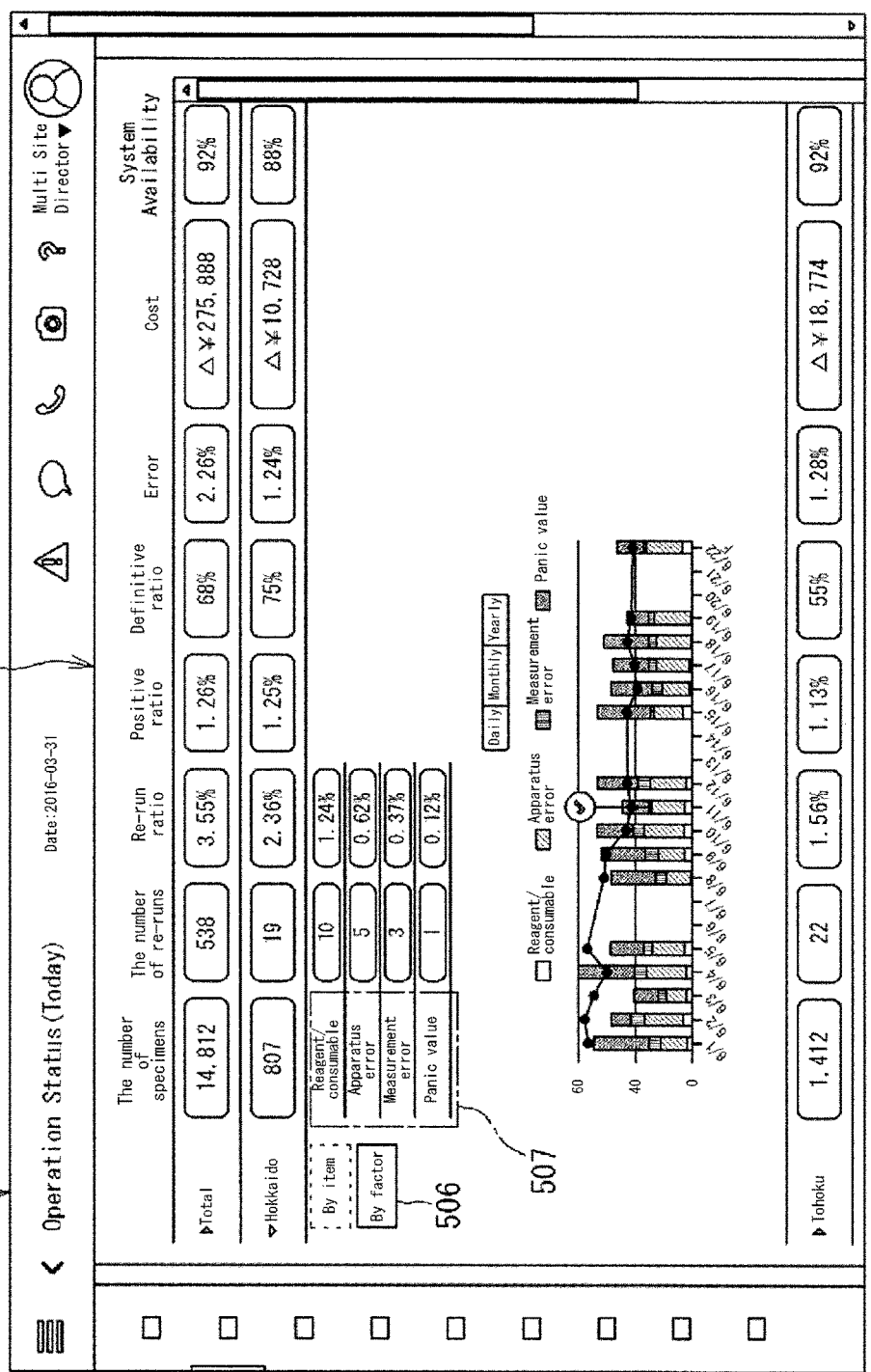
FIG. 26 is a display screen realized by an application.

As shown in FIG. 26, through an operation of selecting a "By factor" button 506 in the display region 500a, the display based on the second hierarchical rank is shown. The second hierarchical rank is allocated to the indexes 502f and 502a. Thus, when the "By factor" button 506 is selected, the value of each index 502f, 502a in Hokkaido is displayed so as to be divided in categories 507 corresponding to the factors above.

The application (ID: B1) calculates the value of each index 502f, 502a, for each abnormality factor set in FIG. 24. In FIG. 26, the abnormality factors include "reagent/consumable", "apparatus error", "measurement error", and "panic value". By referring to the screen shown in FIG. 26, the administrator can ascertain, for each abnormality factor, the indexes 502f and 502a indicating the abnormality occurrence status of the analyzers.

Figure 27:
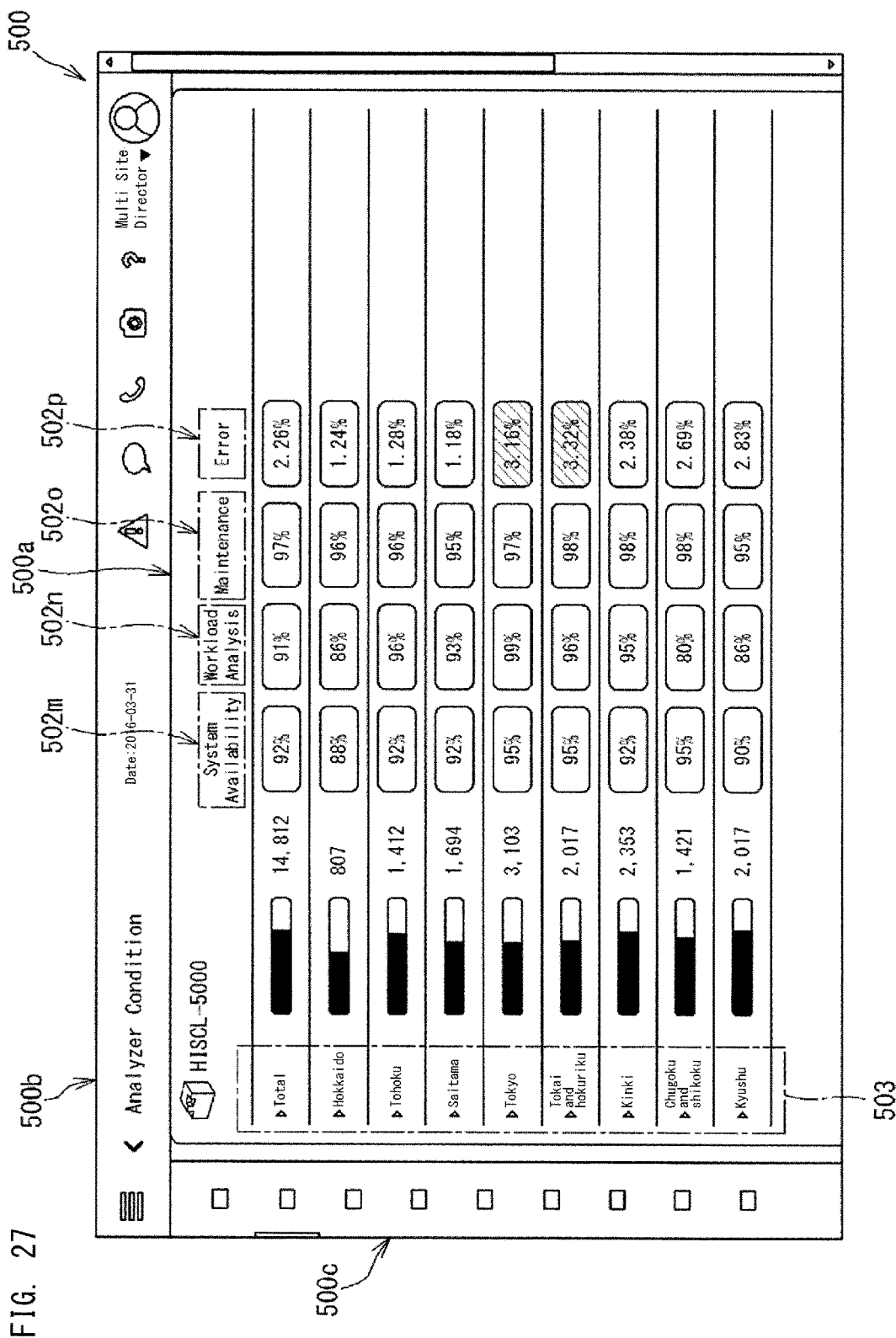
FIG. 27 is a display screen realized by an application.

FIG. 27 shows an example of an application displayed in the display region 500a when an application other than the application 501c displayed in the dashboard 500a is selected. It is assumed that the application being displayed in the dashboard 500a is regarding Analyzer Condition of all the analyzers in the user's area in charge, and that this application displays three indexes of System Availability, Workload Analysis, and Maintenance. When this application (the three indexes) is selected through a user operation, four indexes 502m, 502n, 502o, and 502p, which are respectively System Availability, Workload Analysis, Maintenance, and Error, are displayed in the display region 500a by an application set as the link destination for the selected application, as shown in FIG. 27.

With respect to the application shown in FIG. 27, the four indexes 502m, 502n, 502o, and 502p including the three indexes selected in the dashboard 500a are each displayed so as to be divided in the categories 503 corresponding to a plurality of second regions (Hokkaido, etc.) included in Japan being the administrator's area in charge. The categories 503 are determined with reference to the regions set as the user's area in charge in the user settings information 54a shown in FIG. 18, for example. The values of the indexes 502m, 502n, 502o, and 502p corresponding to the regions are calculated on the basis of the apparatus 10, 11, 12, 13, and 14 installed in the regions. The display by the application shown in FIG. 27 is also useful for the administrator to ascertain the index of each region which is a subdivision of the area in charge, as in the case of the display by the application shown in FIG. 21.

In FIG. 27, when any one of the regions in the categories 503 corresponding to the regions or any one of the indexes 502m, 502n, 502o, and 502p in each region is selected through a user operation, the application shown in FIG. 27 displays each of all the indexes in the selected region, or a specific index in the selected region, so as to be divided for each at least one analyzer installed in the selected region. The division for each at least one analyzer may be a division that includes only one analyzer, or may be a division that includes a plurality of analyzers (for example, clinical laboratory).

Figure 28:
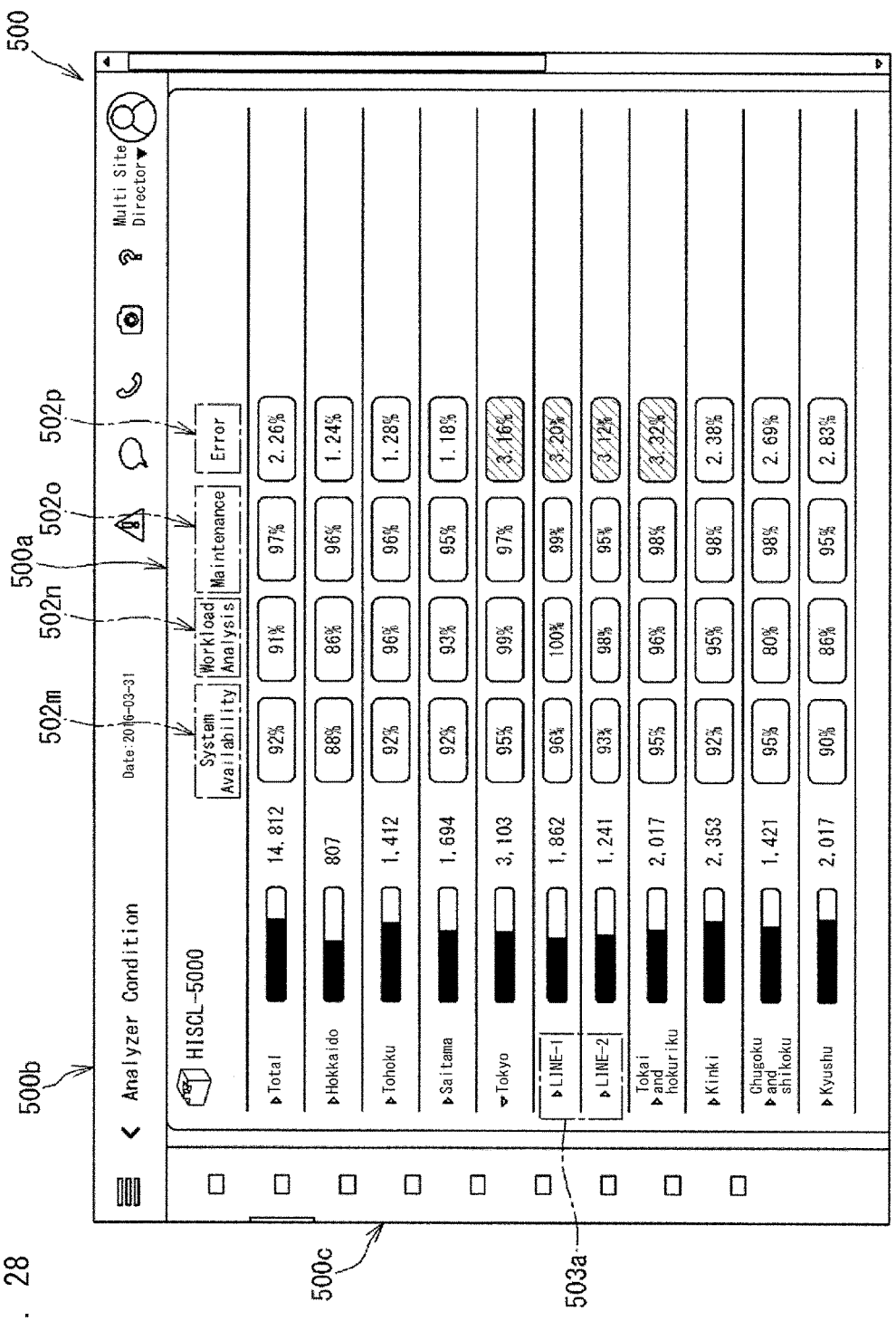
FIG. 28 is a display screen realized by an application.

FIG. 28 shows a case where "Tokyo" has been selected from among the categories 503 corresponding to the regions. In the present embodiment, when "Tokyo" has been selected, all the indexes 502m, 502n, 502o, and 502p in Tokyo are considered to have been selected. With reference to FIG. 28, below "Tokyo" shown in FIG. 27, "LINE-1" and "LINE-2" are additionally displayed, and with respect to each of "LINE-1" and "LINE-2", the indexes 502m, 502n, 502o, and 502p are displayed.

The "LINE" here means a clinical laboratory or the flow of test in a clinical laboratory. One "LINE" includes at least one analyzer. "LINE-1" and "LINE-2" indicate two clinical laboratories present in Tokyo, for example. "LINE" is determined with reference to a clinical laboratory set as the user's area in charge in the user settings information 54a shown in FIG. 18, for example. By referring to the screen shown in FIG. 28, the administrator can ascertain the status of the analyzers in each of the plurality of clinical laboratories in Tokyo.

[3. Benchmark Display]

The controller 51 can cause not only indexes regarding the administrator who is the user logging in but also indexes regarding another administrator, to be displayed as a benchmark in the display region 500a of the terminal 6. Here, the indexes regarding the administrator are indexes to be used by the administrator being the user logging in the Web server 5, in order to manage the clinical laboratories in charge. For example, the indexes shown in FIG. 1, FIG. 19, FIG. 21, and FIG. 25 are indexes regarding the administrator. Another administrator is a user of the management system 100 who is another user viewed from the user logging in the Web server.

Through the display of indexes regarding another administrator, the administrator being the user logging in the Web server can also refer to indexes of sites such as clinical laboratories of which management—the administrator is not in charge. By using, as the benchmark, the indexes of the sites such as clinical laboratories of which management the administrator is not in charge, the administrator can objectively ascertain the status of the clinical laboratories that the administrator manages.

Figure 29:
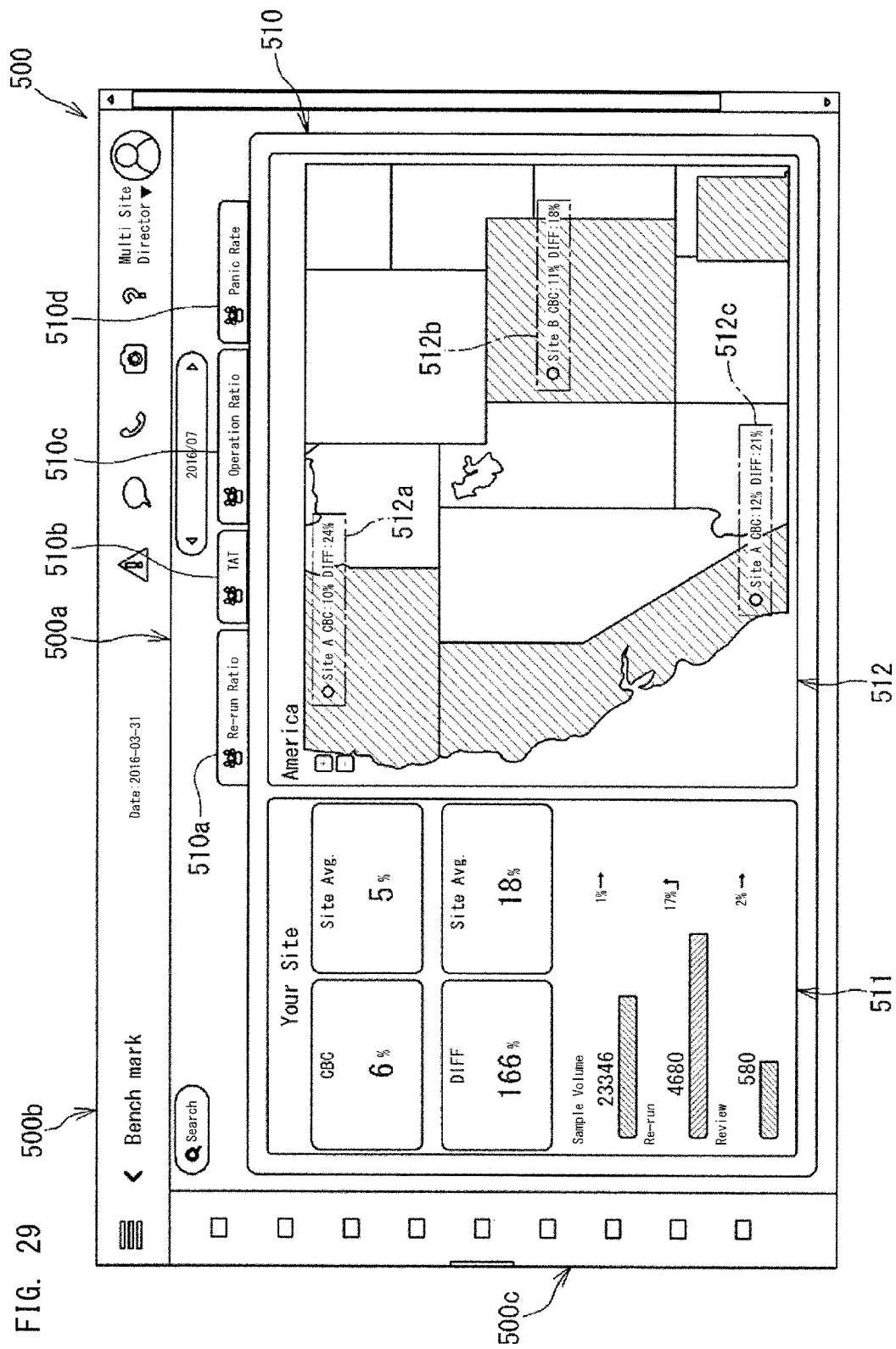
FIG. 29 is a display screen realized by an application.

FIG. 29 shows a screen displayed in the display region 500a in which an index display region 511 regarding the administrator and a benchmark index display region 512 are shown. The display region 500a shown in FIG. 29 is displayed by a benchmark display application. The benchmark display application is included in the applications managed by the application management section 52 of the controller 51.

The benchmark display application is displayed as one widget in the dashboard shown in FIG. 1, for example. Through a user operation of selecting the benchmark display application in the dashboard, the regions 511 and 512 are displayed in the display region 500a.

In the index display region 511 regarding the administrator, displayed are indexes for managing the clinical laboratories of which management the administrator, being the user logging in the Web server 5, is in charge. In the benchmark index display region 512, displayed are indexes of other clinical laboratories (sites) of which management the administrator is not in charge. In the region 512 shown in FIG. 29, indexes 512a, 512b, and 512c in three sites in the United States of America are displayed, respectively.

When a user operation of selecting a tab 510a, 510b, 510c, 510d is made, the indexes displayed in the regions 511 and 512 can be changed. Each selection tab 510a, 510b, 510c, 510d indicates an index to be displayed. For example, since Re-run Ratio 510a has been selected in FIG. 29, indexes regarding the re-run ratio are displayed in the regions 511 and 512. In FIG. 29, the re-run ratio is indicated by indexes that are test item subdivisions (CBC, DIFF, etc.). For example, the region 511 shows that, at the site managed by the administrator, the re-run ratio of the test item CBC is 6% and the re-run ratio of the test item DIFF is 16%. On the other hand, the region 512 shows that, at Site A, the re-run ratio of the test item CBC is 10% and the re-run ratio of the test item DIFF is 24%. Similarly, the region 512 shows that, at Site B, the re-run ratio of the test item CBC is 11% and the re-run ratio of the test item DIFF is 18%; and that, at Site C, the re-run ratio of the test item CBC is 12%, and the re-run ratio of the test item DIFF is 21%. By comparing the displays in the regions 511 and 512, the administrator can more objectively ascertain the status of the site that the administrator manages.

In response to a user operation of selecting an index 512a, 512b, 512c regarding another administrator, the controller 51 may cause the terminal 6 to display the selected index so as to be divided in a plurality of categories. For example, in response to selection of the index 512a at Site A, the controller 51 can cause the selected index (re-run ratio) to be displayed so as to be divided for each plurality of analyzers in Site A.

Preferably, another administrator serving as the benchmark is a person who has permitted information disclosure to the administrator. The permission of information disclosure is set as the user settings information 54a in the user information management section 54, for example. As shown in FIG. 30, in the user settings information 54a for permitting information disclosure, each user is associated with "disclosure to third party permitted?". For example, the settings information 54a in FIG. 30 indicates that a user having the user ID of a001 and a user having the user ID of b001 have each permitted disclosure of information at the site managed by himself/herself to a third party (another administrator), and a user having the user ID of a003 has not permitted disclosure of information at the site managed by himself/herself to a third party (another administrator). In this case, the controller 51 refers to the settings information 54a shown in FIG. 30, and displays, in the region 512, the indexes at the sites managed by the user having the user ID of a001 and the user having the user ID of b001, but does not display, in the region 512, the indexes at the site managed by the user having the user ID of a003.

Figure 31:
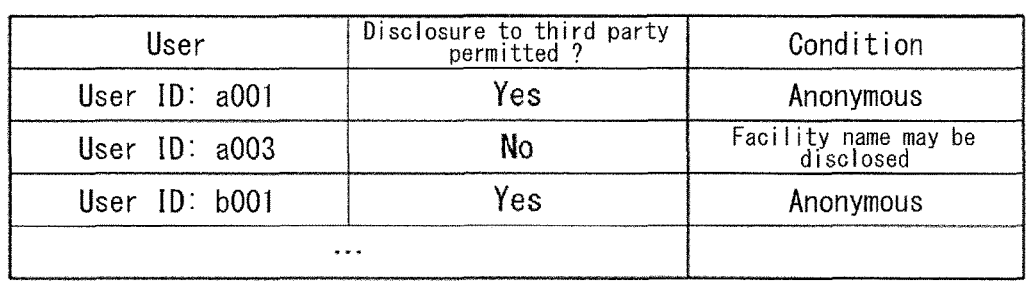
FIG. 31 is a data structure diagram of the settings-information.

As shown in FIG. 31, in the settings information 54a for information disclosure, a condition for information disclosure may be set, in addition to "disclosure to third party permitted?". In the settings information 54a shown in FIG. 31, the user having the user ID of a001 and the user having the user ID of b001 have each permitted disclosure of the information at the site managed by himself/herself to a third party (another administrator), but each have a disclosure condition of "anonymous". In this case, when the controller 51 displays, as the benchmark in the region 512, the indexes at the sites respectively managed by the user having the user ID of a001 and the user having the user ID of b001, the controller 51 does not display specific site names (hospital name, etc.), but display the site name as Site A in anonymous expression, as shown in FIG. 29. The anonymous expression is not limited to the site name, but may be employed for the clinical laboratory name, the kinds/serial numbers of analyzers, and the like.

Registration of the settings information 54a shown in FIGS. 30 and 31 is performed by the administrator of the system 100, on the basis of a declaration made by the user of the system 100, for example. With respect to the declaration, the user of the system 100 makes a declaration to the effect that he/she permits information disclosure to a third party, by sending an e-mail or the like to the administrator of the system 100, for example. The registration of the settings information 54a shown in FIGS. 30 and 31 may be performed by the user of the system 100 logging in the Web server 5 and entering an input to a predetermined interface for information disclosure declaration.

Preferably, in a case where the administrator and another administrator have mutually permitted information disclosure, the controller 51 can display indexes regarding management and indexes regarding another administrator in the display region 500a. FIG. 32 shows an example of the settings information 54a showing users for whom information disclosure have been mutually permitted. In the settings information 54a shown in FIG. 32, for each user, identification information of another user is stored for whom information disclosure is permitted by the user. The settings information 54a in FIG. 32 shows that the user having the user ID of a001 has mutually permitted information disclosure at least among another user having the user ID of a003, another user having the user ID of a004, and another user having the user ID of b001. In this case, by referring to the settings information shown in FIG. 32, when the controller 51 displays indexes regarding the user having the user ID of a003 in the region 511, the controller 51 can display indexes regarding the user having the user ID of a001 in the region 512.

Registration of the settings information 54a shown in FIG. 32 is performed in a similar manner to the registration of the settings information 54a shown in FIGS. 30 and 31. In addition, for registration of the settings information 54a shown in FIG. 32, each user of the system 100 can notify another user of information disclosure requisition, via the system 100. In a case where the another user having received the notification has permitted information disclosure, mutual information disclosure between the user having sent the requisition and the another user having received the requisition is permitted. Alternatively, when the administrator of the system 100 has received a requisition from each user, the administrator may create a host list on the basis of the requisitions. Then, when a host has permitted information disclosure, mutual information disclosure between the requisitioning party and the host may be permitted.

[4. Location-Free Access]

As described above, the administrator being the user can access the Web server 5 via the Web browser of the terminal 6. That is, as long as there is an environment that allows connection to the Internet, the user can access the system 100 even from outside the clinical laboratories to which the user belongs.

When the user has accessed the system 100 from a location outside a clinical laboratory, there is a possibility that information regarding the clinical laboratories managed by the user (the kind/serial number, etc., of analyzers relevant to the clinical laboratories) is viewed by a completely irrelevant third party.

For example, the benchmark display application described above displays information regarding another user of the system 100. Thus, when the user of the terminal 6 has accessed to the system 100 from outside a clinical laboratory to which the user belongs, information regarding another user of the system 100 could be viewed by a completely irrelevant third party.

Therefore, the controller 51 determines a display mode for indexes, etc., to be displayed on the terminal 6, in accordance with the location of the terminal 6. Determination of the display mode can be made in accordance with the access source IP address (information regarding the location of the terminal), as described in step S204 in FIG. 16A, for example. When the user has accessed the Web server 5 from the terminal 6 outside a clinical laboratory, the access source IP address included in the access request is the IP address of a network device outside the clinical laboratory. The controller 51 compares the access source IP address included in the access request with the unlimited IP address of the settings information 54a (FIG. 17A, FIG. 17C) of the user who has made the access. The unlimited IP address in the settings information 54a is the IP address of a network device in the clinical laboratory managed by the administrator being the user or in a workplace of the administrator. If the access source IP address included in the access request matches the unlimited IP address of the settings information 54a (FIG. 17A, FIG. 17C) of the user who has made the access, it is determined that the access is from within the clinical laboratory, and if the access source IP address does not match the unlimited IP address, it is determined that the access is from outside the clinical laboratory.

In a case where the terminal 6 has accessed the Web server 5 from outside the clinical laboratory, the controller 51 displays, in anonymous expression, the clinical laboratory name relevant to the indexes to be displayed, and the kinds/serial numbers, etc., of the analyzers relevant to the clinical laboratory. On the other hand, when the terminal 6 has accessed the Web server 5 from inside the clinical laboratory, the controller 51 displays, not in anonymous expression, the clinical laboratory name relevant to the indexes to be displayed, and the kinds/serial numbers, etc., of the analyzers relevant to the clinical laboratory.

It should be noted that the site names included in the indexes 512a, 512b, and 512c displayed in the region 512 shown in FIG. 29 are not specific hospital names but the names in anonymous expression.

[5. Assessment Progress Status Display]

The controller 51 can cause an assessment progress status of a laboratory technician who belongs to a clinical laboratory managed by the administrator, to be displayed in the display region 500a of the terminal 6. Through the display of the assessment progress status of the laboratory technician, the administrator can easily ascertain the assessment progress status of the laboratory technician being a target of the management.

Figure 33:
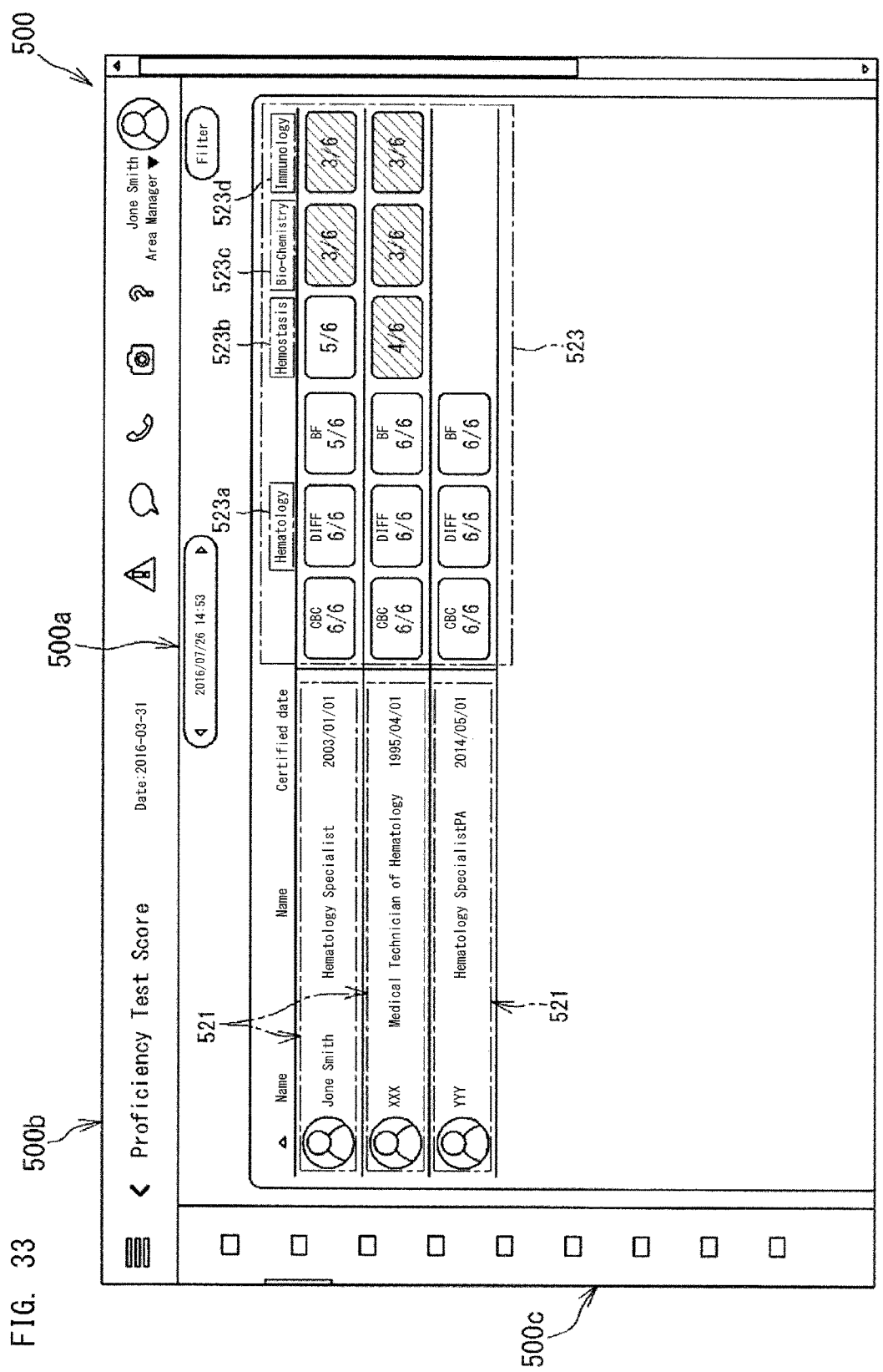
FIG. 33 is a display screen realized by an application.
Figure 35:
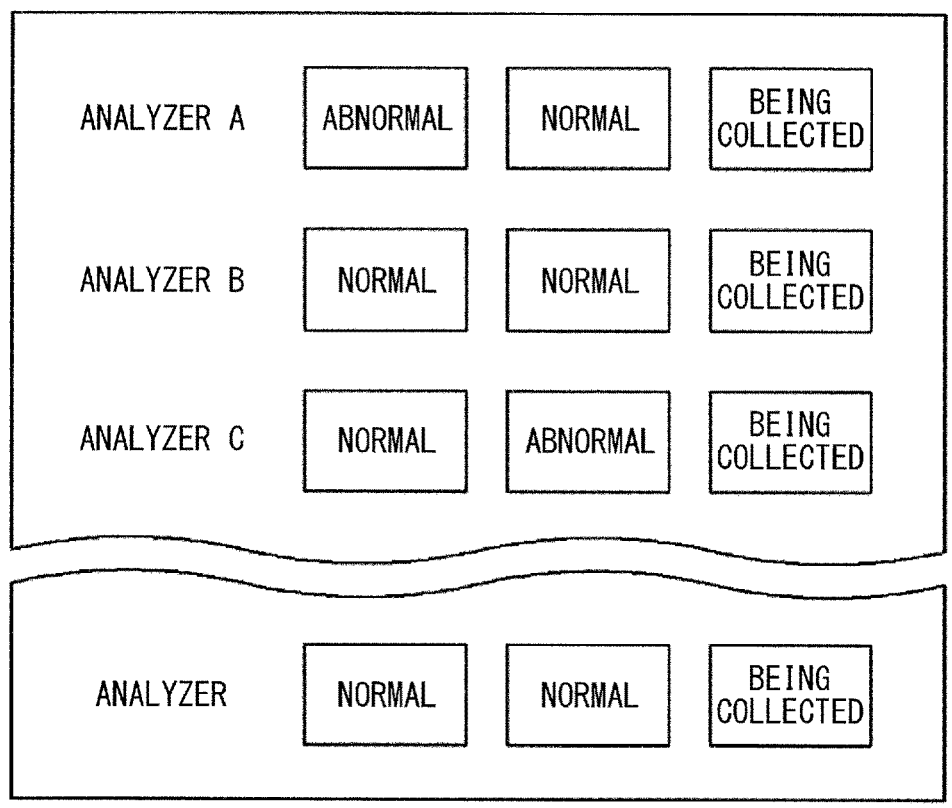
FIG. 35 is a schematic diagram showing a monitor screen according to conventional art.

FIG. 33 shows a screen in which the assessment progress status of laboratory technicians belonging to the clinical laboratories managed by the administrator are displayed in the display region 500a. The assessment means an assessment test which each laboratory technician is required to periodically take under laws and the like. The display region 500a shown in FIG. 33 is displayed by an assessment progress status display application. The assessment progress status display application is included in the applications managed by the application management section 52 of the controller 51.

The assessment progress status display application can be selected through an operation of selecting a menu button displayed in the display regions 500b and 500c, for example. Alternatively, the assessment progress status display application may be displayed as one of the widgets in the dashboard shown in FIG. 1.

In FIG. 33, the assessment progress status display application displays the progress status of the assessment test of each of three laboratory technicians ("Jone Smith", "XXX", and "YYY") 512 belonging to one or plurality of clinical laboratories managed by the administrator ("Jone Smith" shown in FIG. 33). It should be noted that the laboratory technicians may include the administrator. The progress status is displayed for each type of diagnostics 523a, 523b, 523c, 523d in the assessment test. In FIG. 33, Hematology 523a, Hemostasis 523b, Bio-Chemistry 523c, and Immunology 523d are included as the types of diagnostics. With respect to the test progress status for each type of diagnostics, if the laboratory technician has passed four of six mandatory tests, "4/6" is indicated, for example.

The assessment progress status display application is appropriate for an administrator who manages multi-sites. Since the multi-site administrator manages a plurality of clinical laboratories, the multi-site administrator is required to manage the skill of each laboratory technician in each clinical laboratory. By referring to the screen shown in FIG. 33, the administrator can ascertain the assessment progress status of each laboratory technician that the administrator should manage. It should be noted that if the terminal 6 has accessed the Web server 5 from outside the clinical laboratory, the display that corresponds to personal information such as the name of each laboratory technician is displayed in anonymous expression such as "XXX" or "YYY", for example.

In the display region 500a shown in FIG. 33, when a row 521 for displaying the assessment progress of each laboratory technician is selected by being clicked or tapped, the details of the assessment progress of the laboratory technician is displayed in the display region 500a as in FIG. 34. FIG. 33 shows the display region 500a of the case where the row "Tomas Smith" has been selected.

In FIG. 34, the assessment progress status display application displays a score 531 of the assessment test for each fiscal year of the laboratory technician, for each assessment item 530. A score higher than or equal to a reference value and a score lower than the reference value are displayed so as to be distinguishable from each other, by colors or the like. Furthermore, when an icon displayed in the column "Report" is clicked or tapped, detailed report data regarding the assessment test is displayed.

Also in the display shown in FIG. 34, if the terminal 6 has accessed the Web server 5 from outside the clinical laboratory, the display that corresponds to personal information such as the name of each laboratory technician is displayed in anonymous expression.

The score of the assessment test and the data of the report may be collected from a system (information source 1) utilized by each clinical laboratory for human resource information management, or may be those stored in the database 40 by the administrator of each clinical laboratory via the Web server 5.

What is claimed is:

1. An information processing apparatus to be used in management of a clinical laboratory in which an analyzer configured to analyze specimens is installed, the information processing apparatus comprising:
   a communication section configured to communicate with
      a terminal operable by a user; and a controller configured to control display of the terminal via the communication section, wherein the controller is configured to execute:
  a process of causing, on the basis of information collected from a plurality of analyzers installed in one or a plurality of clinical laboratories or from a computer connected to the analyzers, the terminal to display a screen including a first index that indicates a status related to all of the one or the plurality of clinical laboratories; and
  a process of causing, in response to the user selecting the first index displayed in the screen, the terminal to display multiple second indexes illustrating details of the selected first index in a plurality of categories, wherein:
    the first index in the screen indicates a status of specimen analysis performed by the plurality of analyzers, and
    the plurality of categories are categories corresponding to a plurality of test items for tests executed by each of the plurality of analyzers.

2. The information processing apparatus of claim 1, wherein:
  the controller is configured to cause the terminal to display the screen including a plurality of kinds of indexes each indicating a different status related to all of the one or the plurality of clinical laboratories, and to cause, in response to the user selecting at least one of the plurality of kinds of indexes displayed in the screen as the selected first index, the terminal to display the multiple second indexes illustrating details of the selected first index in the plurality of categories.

3. The information processing apparatus of claim 1, wherein:
  the controller is configured to cause, in response to the user selecting the first index in the screen, the terminal to display a third index different from the first index included in the screen, and display multiple fourth indexes illustrating details of the third index in a plurality of categories.

4. The information processing apparatus of claim 1, wherein:
  the first index in the screen indicates a status of all of a plurality of clinical laboratories included in a first region, and
  the plurality of categories are categories corresponding to a plurality of second regions included in the first region.

5. The information processing apparatus of claim 4, wherein:
  the controller is configured to execute a process of causing, in response to the user selecting at least one of the categories corresponding to the plurality of second regions, the terminal to display at least one third index illustrating a detail of the index each at least one analyzer installed in the selected second region.

6. The information processing apparatus of claim 1, wherein:
  the user is an administrator who manages the one or plurality of clinical laboratories, and
  the controller is configured to be able to cause the terminal to display an index regarding the one or the plurality of clinical laboratories managed by the administrator, and an index regarding one or a plurality of clinical laboratories managed by another administrator.

7. The information processing apparatus of claim 6, wherein:
  the controller is configured to be able to cause the terminal to display the index regarding the one or the plurality of clinical laboratories managed by the another administrator who has permitted information disclosure to the administrator.

8. The information processing apparatus of claim 7, wherein:
  the controller is configured to be able to cause the terminal to display the index regarding the one or the plurality of clinical laboratories managed by the another administrator in a case where the administrator and the another administrator have mutually permitted information disclosure.

9. The information processing apparatus of claim 1, wherein:
  the controller is configured to determine a display mode for the first index on the basis of information regarding a location of the terminal.

10. The information processing apparatus of claim 1, wherein:
  the controller is configured to automatically update the display of the terminal in response to change in the status of the one or the plurality of clinical laboratories, the display corresponding to the first index in the screen.

11. The information processing apparatus of claim 1, wherein:
  the controller is configured to cause the terminal to display the first index with reference to a database which manages in a centralized manner the information collected from the plurality of analyzers or the computer connected to the analyzers.

12. The information processing apparatus of claim 1, wherein:
  the controller is configured to be able to set, for each user of a plurality of users, an index for that user that is to be displayed by the terminal.

13. The information processing apparatus of claim 12, wherein:
  the first index to be displayed by the terminal can be set by the user.

14. The information processing apparatus of claim 1, wherein:
  the communication section is capable of communicating with the terminal that has a touch panel operable by the user, and
  the controller is configured:
    to cause the touch panel to display the first index in a form of an icon; and
    to cause, in response to the user tapping the first index displayed in the form of an icon, the touch panel to display the multiple second indexes illustrating details of the tapped first index in a plurality of categories.

15. The information processing apparatus of claim 1, wherein:
  the controller is configured to be able to automatically adjust, in accordance with a screen size of the terminal, arrangement of the first index to be displayed on the terminal and a display size of the first index.

16. The information processing apparatus of claim 1, wherein:
  the first index is selected from a group consisting of:
    a turnaround time (TAT) per specimen in the entirety of the one or the plurality of clinical laboratories;
    a load status of the analyzers in the entirety of the one or the plurality of clinical laboratories;

availability of the analyzers in the entirety of the one or the plurality of clinical laboratories;
a status of occurrence of abnormality in the analyzers in the entirety of the one or the plurality of clinical laboratories; and
an operation status of the analyzers in the entirety of the one or the plurality of clinical laboratories.

17. The information processing apparatus of claim 1, wherein:
the user is an administrator who manages the one or the plurality of clinical laboratories, and
the controller is configured to be able to cause the terminal to display an assessment progress status of a laboratory technician managed by the administrator.

18. The information processing apparatus of claim 1, wherein:
the plurality of analyzers are each configured to analyze specimens for at least one common test item.

19. A management method for a clinical laboratory in which an analyzer configured to analyze specimens is installed, the method comprising:
on the basis of information collected from a plurality of analyzers installed in one or a plurality of clinical laboratories or from computers connected to the analyzers, displaying to a user a screen including a first index that indicates a status related to all of the one or the plurality of clinical laboratories; and
in response to the user selecting the first index displayed in the screen, displaying to the user multiple second indexes illustrating details of the selected first index in a plurality of categories, wherein:
the first index in the screen indicates a status of occurrence of abnormality in the plurality of analyzers, and
the plurality of categories are categories corresponding to factors of the abnormality.

20. The management method of claim 19, wherein:
in response to the user selecting the first index in the screen, displaying to the user a third index different from the first index in the screen and multiple fourth indexes illustrating details of the third index in a plurality of categories.

21. The management method of claim 19, wherein:
the first index in the screen indicates a status of all of a plurality of clinical laboratories included in a first region, and
the plurality of categories are categories corresponding to a plurality of second regions included in the first region.

22. The management method of claim 19, wherein:
the user is an administrator who manages the one or the plurality of clinical laboratories, and
a screen including an index regarding the one or the plurality of clinical laboratories managed by the administrator and an index regarding one or a plurality of clinical laboratories managed by another administrator is displayed to the administrator.

23. The management method of claim 19, further comprising:
determining a display mode for the first index in accordance with a location of the user.

24. An information processing apparatus to be used in management of a clinical laboratory in which an analyzer configured to analyze specimens is installed, the information processing apparatus comprising:
a communication section configured to communicate with a terminal operable by a user; and
a controller configured to control display of the terminal via the communication section, wherein the controller is configured to execute:
a process of causing, on the basis of information collected from a plurality of analyzers installed in one or a plurality of clinical laboratories or from a computer connected to the analyzers, the terminal to display a screen including a first index that indicates a status related to all of the one or the plurality of clinical laboratories; and
a process of causing, in response to the user selecting the first index displayed in the screen, the terminal to display multiple second indexes illustrating details of the selected first index in a plurality of categories, wherein:
the user is an administrator who manages the one or the plurality of clinical laboratories, and
the controller is configured to be able to cause the terminal to display an index regarding the one or the plurality of clinical laboratories managed by the administrator, and an index regarding one or a plurality of clinical laboratories managed by another administrator.

25. The information processing apparatus of claim 24, wherein:
the controller is configured to be able to cause the terminal to display the index regarding the one or the plurality of clinical laboratories managed by the another administrator who has permitted information disclosure to the administrator.

26. The information processing apparatus of claim 25, wherein:
the controller is configured to be able to cause the terminal to display the index regarding the one or the plurality of clinical laboratories managed by the another administrator in a case where the administrator and the another administrator have mutually permitted information disclosure.

27. An information processing apparatus to be used in management of a clinical laboratory in which an analyzer configured to analyze specimens is installed, the information processing apparatus comprising:
a communication section configured to communicate with a terminal operable by a user; and
a controller configured to control display of the terminal via the communication section, wherein the controller is configured to execute:
a process of causing, on the basis of information collected from a plurality of analyzers installed in one or a plurality of clinical laboratories or from a computer connected to the analyzers, the terminal to display a screen including a first index that indicates a status related to all of the one or the plurality of clinical laboratories; and
a process of causing, in response to the user selecting the first index displayed in the screen, the terminal to display multiple second indexes illustrating details of the selected first index in a plurality of categories, wherein:
the first index in the screen indicates a status of all of a plurality of clinical laboratories included in a first region, and
the plurality of categories are categories corresponding to a plurality of second regions included in the first region.

28. The information processing apparatus of claim 27, wherein:

the controller is configured to execute a process of causing, in response to the user selecting at least one of the categories corresponding to the plurality of second regions, the terminal to display at least one third index illustrating a detail of the index for each at least one analyzer installed in the selected second region.

29. An information processing apparatus to be used in management of a clinical laboratory in which an analyzer configured to analyze specimens is installed, the information processing apparatus comprising:
  a communication section configured to communicate with a terminal operable by a user; and
  a controller configured to control display of the terminal via the communication section, wherein the controller is configured to execute:
    a process of causing, on the basis of information collected from a plurality of analyzers installed in one or a plurality of clinical laboratories or from a computer connected to the analyzers, the terminal to display a screen including a first index that indicates a status related to all of the one or the plurality of clinical laboratories; and
    a process of causing, in response to the user selecting the first index displayed in the screen, the terminal to display multiple second indexes illustrating details of the selected first index in a plurality of categories;
  wherein the controller is configured to be able to set, for each user of a plurality of users, an index for that user that is to be displayed by the terminal.

30. The information processing apparatus of claim 29, wherein:
  the first index to be displayed by the terminal can be set by the user.

31. A management method for a clinical laboratory in which an analyzer configured to analyze specimens is installed, the method comprising:
  on the basis of information collected from a plurality of analyzers installed in one or a plurality of clinical laboratories or from computers connected to the analyzers, displaying to a user a screen including a first index that indicates a status related to all of the one or the plurality of clinical laboratories; and
  in response to the user selecting the first index displayed in the screen, displaying to the user multiple second indexes illustrating details of the selected first index in a plurality of categories, wherein:
    the first index in the screen indicates a status of specimen analysis performed by the plurality of analyzers, and
    the plurality of categories are categories corresponding to a plurality of test items for tests executed by each of the plurality of analyzers.

32. An information processing apparatus to be used in management of a clinical laboratory in which an analyzer configured to analyze specimens is installed, the information processing apparatus comprising:
  a communication section configured to communicate with a terminal operable by a user; and
  a controller configured to control display of the terminal via the communication section, wherein the controller is configured to execute:
    a process of causing, on the basis of information collected from a plurality of analyzers installed in one or a plurality of clinical laboratories or from a computer connected to the analyzers, the terminal to display a screen including a first index that indicates a status related to all of the one or the plurality of clinical laboratories; and
    a process of causing, in response to the user selecting the first index displayed in the screen, the terminal to display multiple second indexes illustrating details of the selected first index in a plurality of categories, wherein:
      the first index in the screen indicates a status of occurrence of abnormality in the plurality of analyzers, and
      the plurality of categories are categories corresponding to factors of the abnormality.

33. An information processing apparatus to be used in management of a clinical laboratory in which an analyzer configured to analyze specimens is installed, the information processing apparatus comprising:
  a communication section configured to communicate with a terminal operable by a user; and
  a controller configured to control display of the terminal via the communication section, wherein the controller is configured to execute:
    a process of causing, on the basis of information collected from a plurality of analyzers installed in one or a plurality of clinical laboratories or from a computer connected to the analyzers, the terminal to display a screen including a first index that indicates a status related to all of the one or the plurality of clinical laboratories; and
    a process of causing, in response to the user selecting the first index displayed in the screen, the terminal to display multiple second indexes illustrating details of the selected first index in a plurality of categories;
  wherein the controller is configured to determine a display mode for the first index on the basis of information regarding a location of the terminal.

* * * * *